(12) United States Patent
Adamus et al.

(10) Patent No.: US 9,260,506 B2
(45) Date of Patent: Feb. 16, 2016

(54) TREATMENT OF RETINAL DISORDERS WITH RECOMBINANT T CELL RECEPTOR LIGAND (RTL)

(75) Inventors: Grazyna Adamus, Tigard, OR (US); Arthur A. Vandenbark, Portland, OR (US)

(73) Assignees: Oregon Health & Science University, Portland, OR (US); The United States of America as represented by the Department of Veterans Affairs, Washington, DC (US)

(*) Notice: Subject to any disclaimer, the term of this patent is extended or adjusted under 35 U.S.C. 154(b) by 749 days.

(21) Appl. No.: 13/441,719

(22) Filed: Apr. 6, 2012

(65) Prior Publication Data
US 2012/0276127 A1 Nov. 1, 2012

Related U.S. Application Data

(60) Provisional application No. 61/516,918, filed on Apr. 7, 2011.

(51) Int. Cl.
*A61K 38/00* (2006.01)
*C07K 14/74* (2006.01)
*A61K 39/00* (2006.01)
*A61K 38/17* (2006.01)

(52) U.S. Cl.
CPC ....... *C07K 14/70539* (2013.01); *A61K 38/1774* (2013.01); *A61K 39/0008* (2013.01); *C07K 2319/00* (2013.01); *C07K 2319/32* (2013.01)

(58) Field of Classification Search
None
See application file for complete search history.

(56) References Cited

U.S. PATENT DOCUMENTS

| | | | | |
|---|---|---|---|---|
| 6,270,772 | B1 * | 8/2001 | Burrows et al. | 424/193.1 |
| 2003/0007978 | A1 | 1/2003 | Burrows et al. | |
| 2005/0142142 | A1 * | 6/2005 | Burrows et al. | 424/185.1 |
| 2009/0280135 | A1 * | 11/2009 | Offner et al. | 424/184.1 |
| 2011/0008382 | A1 * | 1/2011 | Burrows et al. | 424/192.1 |

FOREIGN PATENT DOCUMENTS

WO    WO 96/40944    12/1996

OTHER PUBLICATIONS

Adamus et al.,Ophthalmic Res. 2010;44(1):24-33. doi: 10.1159/000281815. Epub Feb. 8, 2010.*
Hayreh et al., Invest Ophthalmol Vis Sci. Aug. 1981;21(2):256-69.*
Vandenbark et al., J Immunol. Jul. 1, 2003;171(1):127-33.*
Adamus and Chan, "Experimental autoimmune uveitides: multiple antigens, diverse diseases," *Int. Rev. Immunol.* vol. 21, pp. 209-229, 2002.
Adamus et al., "Treatment of autoimmune anterior uveitis with recombinant TCR ligands," *Invest. Ophthalmol. Vis. Sci.* Vo. 47, pp. 2555-2561, 2006.
Adamus et al., "A promising therapeutic approach for treatment of posterior uveitis: recombinant T cell receptor ligand protects Lewis rats from acute and recurrent experimental autoimmune uveitis," *Ophthalmic Res.* vol. 44, pp. 24-33, 2010.
Adamus, "Immunotherapy with Recombinant T-cell Receptor Ligand (RTL) for Retinal Degeneration," available on the World Wide Web at http://www.ohsu.edu/xd/research/centers-institutes/octri/funding/upload/Adamus_abstract.pdf, 2010 (Abstract, 1 page).
Adamus et al. "Antigen-Specific Immunotherapy Protects Optic Nerve from Inflammation and Demyelination in "Humanized" HLA-DR2 Mice with Optic Neuritis," ARVO 2011 Meeting, 2011 (Abstract, 2 pages).
Adamus et al., "Neuroprotective Effects of Recombinant T-cell Receptor Ligand in Autoimmune Optic Neuritis is HLA-DR2 Mice," *Invest. Ophthalmol. Vis. Sci.* vol. 53, pp. 406-412, 2011.
Burrows et al., "Design, Engineering and Production of Functional Single-Chain T Cell Receptor Ligands," *Protein Eng.* vol. 12, pp. 771-778, 1999.
Chang et al. "Design, Engineering, and Production of Human recombinant T Cell Receptor Ligands Derived from Human Leukocyte Antigen DR2," *J. Biol. Chem.*, vol. 276, pp. 24170-24176, 2001.
Huan et al. "Rationally designed mutations convert complexes of human recombinant T cell receptor ligands into monomers that retain biological activity," *J. Chem. Technol. Biotechnol.*, vol. 80, pp. 2-12, 2005.
Kezuka et al., "Peptide-mediated suppression of experimental autoimmune uveoretinitis in mice: development of a peptide vaccine," *Int. Immunol.* vol. 8, pp. 1229-1235, 1996.
Sanui et al., "Identification of an Immunodominant and Highly Immunopathogenic Determinant in the Retinal Interphotoreceptor Retinoid-Binding Protein (IRBP)," *J. Exp. Med.* vol. 169, pp. 1947-1960, 1989.
Sasamoto et al., "Immunomodulation of experimental autoimmune uveoretinitis by intravenous injection of uveitogenic peptides," *Invest. Ophthalmol. Vis. Sci.* vol. 33, pp. 2641-2649, 1992.
Wildner et al., "Rat models of autoimmune uveitis," *Ophthalmic Res.* vol. 40, pp. 141-144, 2008.

* cited by examiner

*Primary Examiner* — Michael Szperka
(74) *Attorney, Agent, or Firm* — Klarquist Sparkman, LLP

(57) ABSTRACT

Methods are provided for the treatment of a retinal disorder or optic neuritis in a subject. In some embodiments, the methods include administering a therapeutically effective amount of an MHC molecule including covalently linked first, second, and third domains; wherein the first domain is an MHC class II β1 domain and the second domain is an MHC class II α1 domain, wherein the amino terminus of the α1 domain is covalently linked to the carboxy terminus of the β1 domain; or wherein the first domain is an MHC class I α1 domain and the second domain is an MHC class I α2 domain, wherein the amino terminus of the α2 domain is covalently linked to the carboxy terminus of the α1 domain; and wherein the third domain is covalently linked to the first domain and comprises a retinal antigen or an antigen of the central or peripheral nervous system.

21 Claims, 13 Drawing Sheets
(7 of 13 Drawing Sheet(s) Filed in Color)

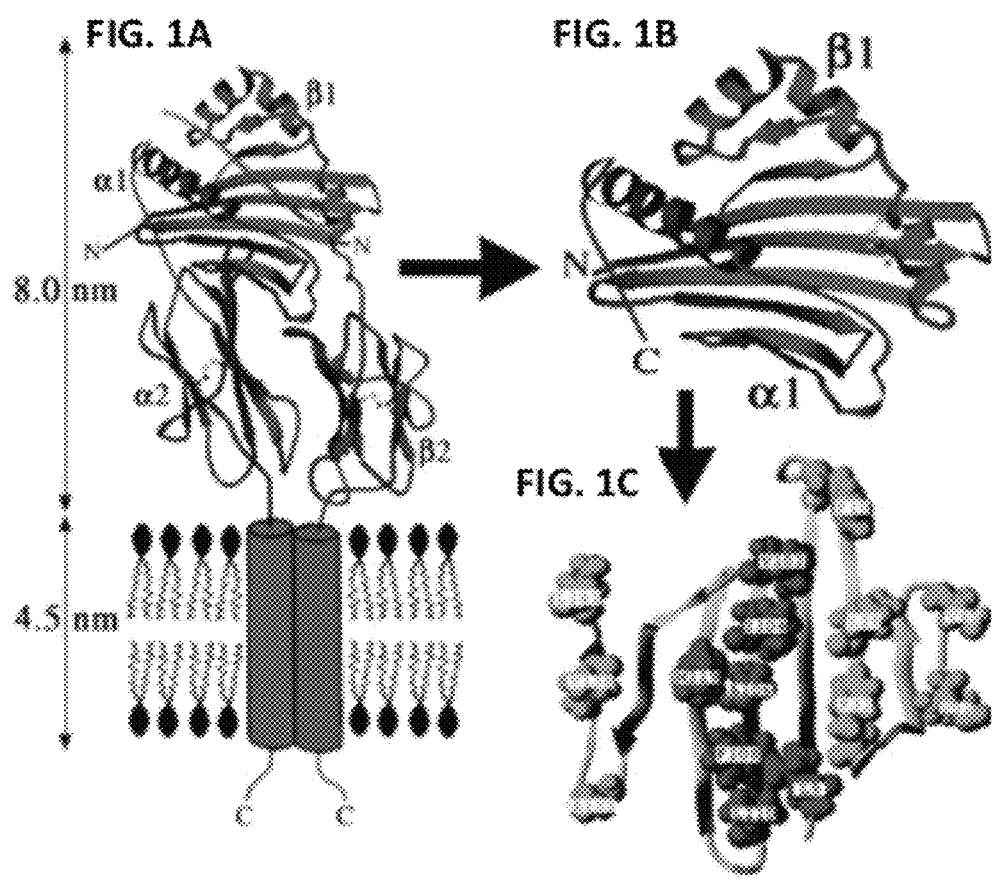

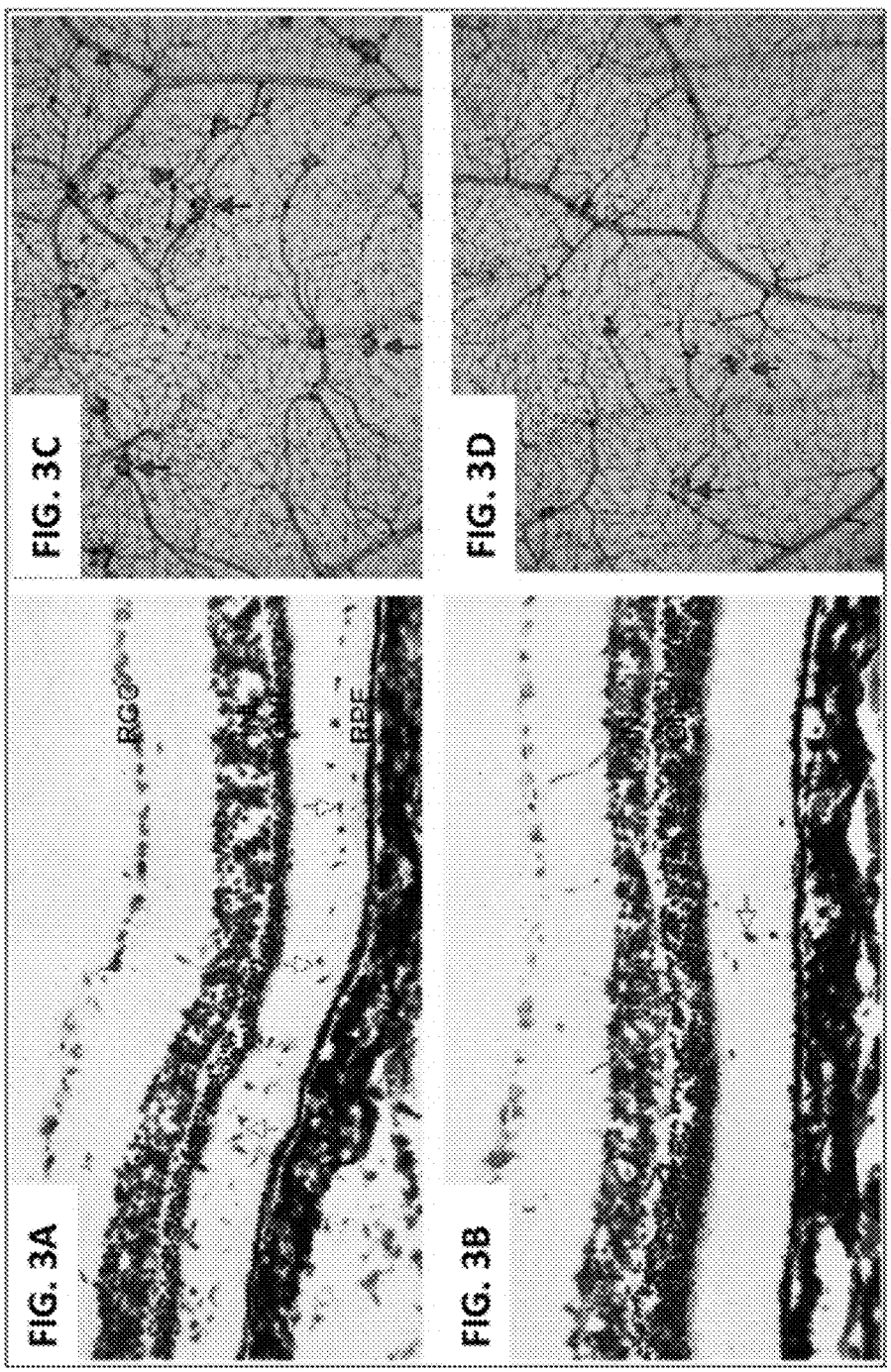

Onset of ON day 8 PI

FIG. 7A
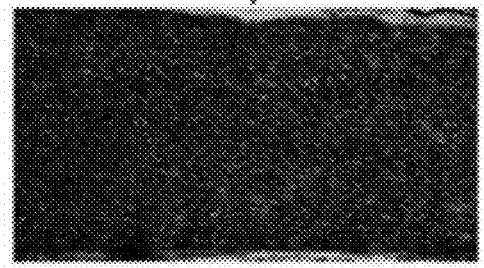
Normal Optic Nerve
FIG. 7B  FIG. 7C
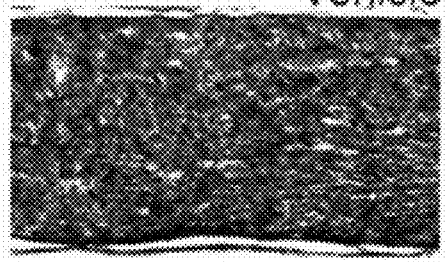  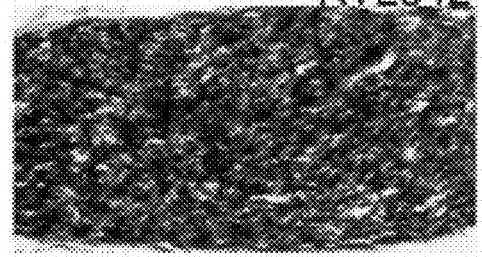
Vehicle  RTL342
16 PI
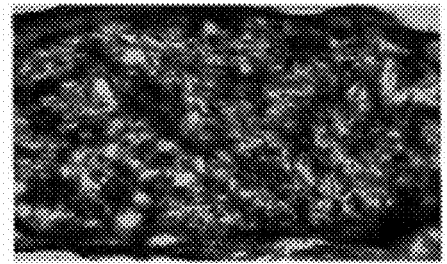  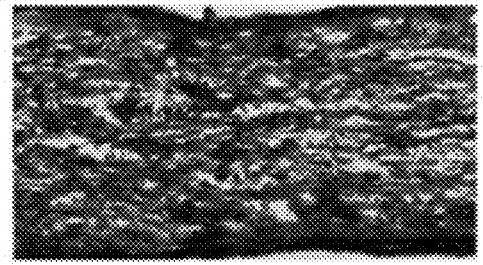
30 PI
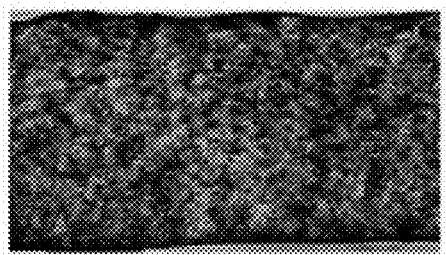  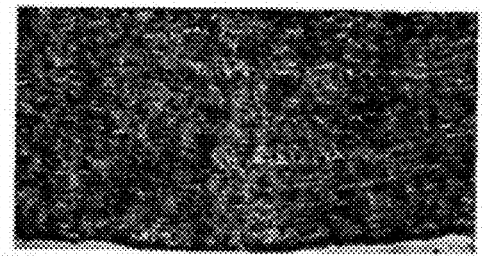
62 PI FIG. 7D
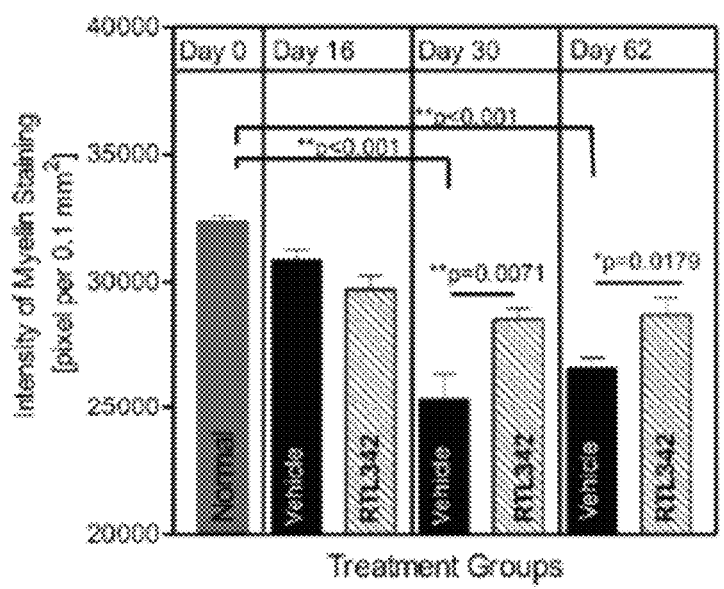
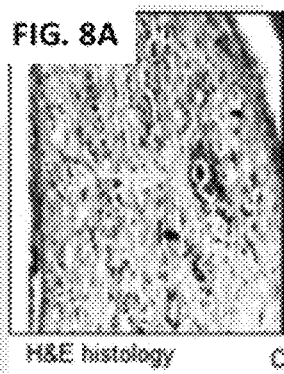
H&E histology
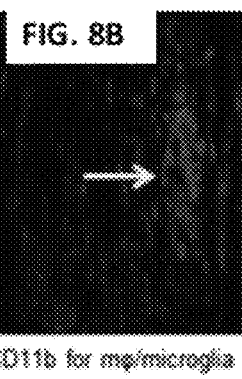
CD11b for mp/microglia
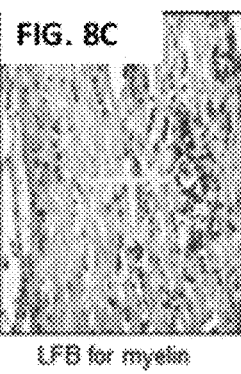
LFB for myelin
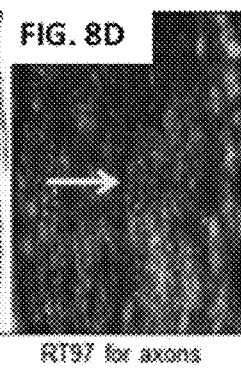
RT97 for axons

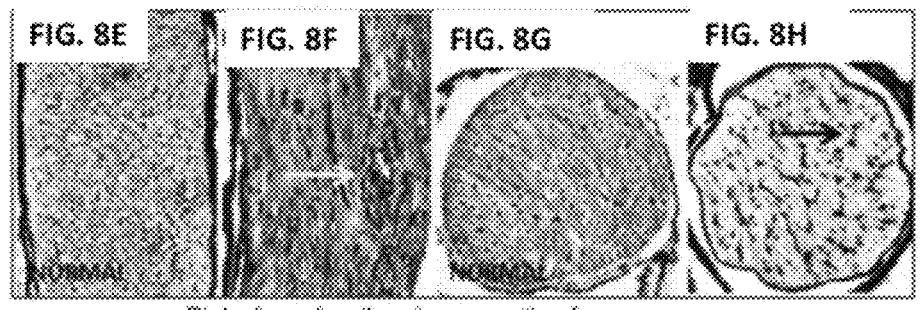
Bielschowsky silver impregnation for axons
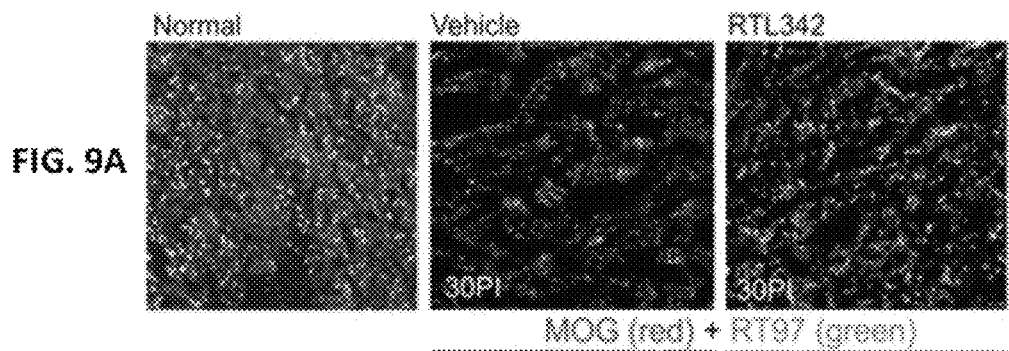
FIG. 9A
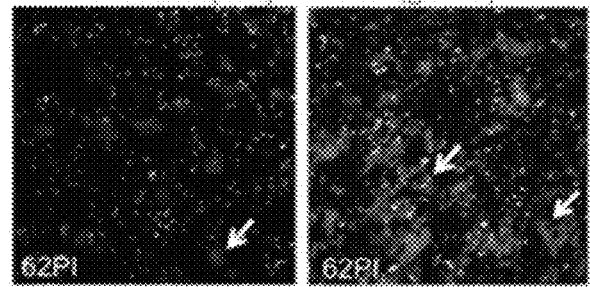
FIG. 9B
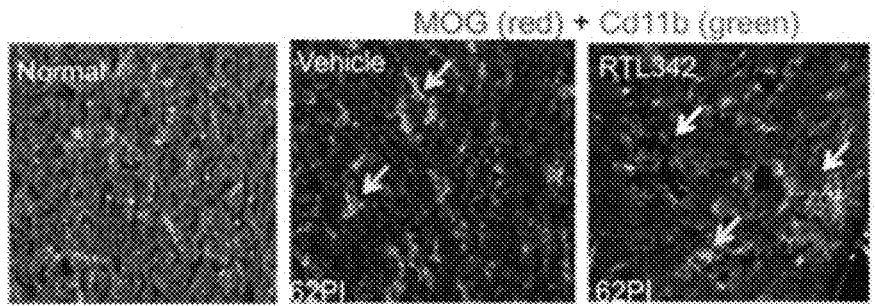

TREATMENT OF RETINAL DISORDERS WITH RECOMBINANT T CELL RECEPTOR LIGAND (RTL)

CROSS REFERENCE TO RELATED APPLICATION

This claims the benefit of U.S. Provisional Application No. 61/516,918, filed Apr. 7, 2011, which is incorporated by reference herein in its entirety.

ACKNOWLEDGMENT OF GOVERNMENT SUPPORT

This invention was made with government support under grant numbers 5ULIRR024140-04, EY17781, and NS047661 awarded by the National Institutes of Health. The government has certain rights in the invention.

FIELD

This disclosure relates to retinal and other eye disorders, and particularly to methods of treating ophthalmic conditions, such as retinal degeneration or optic neuritis, for example utilizing recombinant T cell receptor ligands.

BACKGROUND

Retinal degeneration is a major characteristic of retinitis pigmentosa (RP), age-related macular degeneration (AMD), autoimmune retinopathy (AR), and other related retinal diseases. The common end outcome of all forms of degenerative diseases is photoreceptor cell death and loss of visual function. As photoreceptors degenerate, secondary changes, including vascular leakage, exacerbate visual loss leading to blindness (Milam et al., *Prog. Retin. Eye Res.* 17:175-205, 1998; Grunwald et al., *Am. J. Ophthalmol.* 122:502-508, 1996). The mechanism leading to development of these diseases remains largely unknown and appears to be complex, likely caused by combinations of genetic and cellular factors that affect not only the disease itself but also its response to various treatments (Nussenblatt and Ferris, *Am. J. Ophthalmol.* 144:618-626, 2007; Reme et al., *Documenta Ophthalmologica* 106:25-29, 2003).

Treatment options for these conditions remain limited. Currently, the therapeutic approach is restricted to slowing down the degenerative process by sunlight protection and vitamin therapy, treating complications (such as cataract and macular edema), and helping patients to cope with the social and psychological impact of blindness. Gene therapy has been shown to be effective in a few RP patients with specific gene mutations, but there is no effective therapy that stops the development of the disease or restores the vision, so the visual prognosis is poor. At present, the most effective proven therapy for AMD is repeated intravitreal injection administration of humanized antibodies against vascular endothelial growth factor (VEGF); however, such injections have a high risk of complications.

Optic neuritis is an inflammation of the optic nerve. This condition usually presents with sudden onset of vision loss, typically in one eye. Other symptoms include pain on eye movement, altered color vision, and decreased pupillary light reaction. Recovery of visual acuity generally occurs over a period of weeks to months; however, color vision, contrast sensitivity, and light brightness sensitivity abnormalities may persist. Treatments for optic neuritis vary depending on the specific etiology, but corticosteroids are often effective.

SUMMARY

Methods are provided herein for the treatment of a retinal disorder (such as retinal degeneration, retinitis pigmentosa, macular degeneration, or autoimmune retinopathy) in a subject. Also provided are methods for the treatment of optic neuritis in a subject.

In some embodiments, methods of treating a retinal disorder in a subject include selecting a subject with a retinal disorder and administering to the subject a therapeutically effective amount of a major histocompatibility complex (MHC) molecule including covalently linked first, second, and third domains; wherein the first domain is an MHC class II $\beta 1$ domain and the second domain is an MHC class II $\alpha 1$ domain, wherein the amino terminus of the $\alpha 1$ domain is covalently linked to the carboxy terminus of the $\beta 1$ domain; or wherein the first domain is an MHC class I $\alpha 1$ domain and the second domain is an MHC class I $\alpha 2$ domain, wherein the amino terminus of the $\alpha 2$ domain is covalently linked to the carboxy terminus of the $\alpha 1$ domain; and wherein the third domain is covalently linked to the first domain and comprises a retinal antigen, thereby treating the retinal disorder in the subject. In some examples, the MHC molecule does not include an MHC class II $\alpha 2$ domain or an MHC class II $\beta 2$ domain. In other examples, the MHC molecule does not include an MHC class I $\alpha 3$ domain.

In other embodiments, methods of treating optic neuritis in a subject include selecting a subject with optic neuritis and administering to the subject a therapeutically effective amount of an MHC molecule including covalently linked first, second, and third domains; wherein the first domain is an MHC class II $\beta 1$ domain and the second domain is an MHC class II $\alpha 1$ domain, wherein the amino terminus of the $\alpha 1$ domain is covalently linked to the carboxy terminus of the $\beta 1$ domain; or wherein the first domain is an MHC class I $\alpha 1$ domain and the second domain is an MHC class I $\alpha 2$ domain, wherein the amino terminus of the $\alpha 2$ domain is covalently linked to the carboxy terminus of the $\alpha 1$ domain; and wherein the third domain is covalently linked to the first domain and comprises an antigen of the central or peripheral nervous system, thereby treating the optic neuritis in the subject. In some examples, the MHC molecule does not include an MHC class II $\alpha 2$ domain or an MHC class II $\beta 2$ domain. In other examples, the MHC molecule does not include an MHC class I $\alpha 3$ domain.

In some embodiments, the subject is a human subject. In some examples, the subject does not have uveitis. In other examples, the subject does not have multiple sclerosis (for example, does not have multiple sclerosis at the time of diagnosis with the retinal disorder or optic neuritis). In particular examples, the retinal disorder is a retinal degeneration (such as retinitis pigmentosa or macular degeneration). In other examples, the retinal disorder is a retinopathy (such as autoimmune retinopathy or diabetic retinopathy). In further examples, the retinal disorder is optic neuritis.

In some embodiments, the antigen is covalently linked to the amino terminus of the first domain of the MHC molecule (for example by a peptide bond). In some examples, the antigen is covalently linked to the first domain of the MHC molecule by a peptide linker. In other examples, the antigen is covalently linked to the first domain of the MHC molecule by a disulfide bond. In some embodiments, the antigen includes a retinal antigen, such as interphotoreceptor retinoid binding protein (IRBP), arrestin (S-antigen), recoverin, rhodopsin, phosducin, or an antigenic determinant thereof. In other embodiments, the antigen includes an antigen of the central or peripheral nervous system such as a myelin protein (for example, myelin oligodendrocyte glycoprotein (MOG), myelin basic protein (MBP), or proteolipid protein (PLP)), or an antigenic determinant thereof.

In some embodiments, the disclosed methods further include measuring visual function, retinal function, or retinal structure (such as visual acuity, visual discrimination, visual field, color vision, electroretinogram (ERG), Amsler grid, fundus examination, fluorescein angiography, or optical coherence tomography (OCT)) of the subject. The methods may further include administering an additional therapy to the subject, such as gene therapy, vitamin or mineral supplements, anti-angiogenic therapy, photocoagulation, photodynamic therapy, lutein or zeaxanthin, corticosteroids, or immunosuppressants.

The foregoing and other features of the disclosure will become more apparent from the following detailed description, which proceeds with reference to the accompanying figures.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 1A-C is a series of diagrams showing the predicted structure of MHC class II polypeptides. FIG. 1A is a model of an HLA-DR2 polypeptide on the surface of an antigen presenting cell (APC). FIG. 1B is a model of an exemplary MHC class II β1α1 molecule. FIG. 1C is a model of an exemplary β-sheet platform from a HLA-DR2 β1α1 molecule showing the hydrophobic residues.

FIG. 2A shows retina at postnatal day (P) 30 in untreated RCS rat, showing activation of microglia in the outer retina. FIG. 2B shows retina at P60 in untreated RCS rat showing an increase in microglia in the subretinal space. FIG. 2C shows retina at P60 in RCS rat treated with control (empty) RTL101. FIG. 2D shows retina at P60 in RCS rat treated with RTL220. RTL220 decreased microglia and preserved significant photoreceptors. RGC, retinal ganglion cell layer; INL, inner nuclear layer; ONL, outer nuclear layer; RPE, retinal pigment epithelium.

FIG. 3A-D is a series of digital images of RCS rat retinas at P60 (FIGS. 3A and 3B) or P90 (FIGS. 3C and 3D) treated with control (empty) RTL101 or RTL220. Cresyl violet staining demonstrated that the control treated rats showed typical degeneration with microglial cell infiltration in the subretinal space (arrows; FIG. 3A), while RTL220 treated retinas did not show substantial subretinal microglial cell infiltration (arrow; FIG. 3B) and the ONL was about 8 cells deep, compared with 3-4 cells deep in control treated rats. Retinal whole mount of RCS rat retina stained with NADPH showed more pathologic vascular complexes (arrows) in the control retina (FIG. 3C) compared with the RTL220 treated retina (FIG. 3D).

FIG. 5A is a graph of the time course of ON in HLA-DR2 mice based on three experiments determined using longitudinal sections of the optic nerve stained with H&E. FIG. 5B is a digital image of histopathology of representative ON at onset. H&E staining of the cross-section (top) and longitudinal section (bottom). Arrows indicate inflammatory cells. FIG. 5C is a graph showing clinical time course of EAE in vehicle- and RTL342M-treated HLA-DR2 mice. Top arrows indicate the time of tissue collection; bottom arrows indicate the time of treatment administration (five doses of 20 µg RTL342M/dose on consecutive days starting at onset of ON). FIG. 5D is a bar graph showing severity of ON in vehicle- and RTL342M-treated mice at days 16, 30 and 62 post-immunization (PI).

FIG. 7A-D is a series of panels showing myelin loss in optic nerves of RTL342M- and vehicle-treated HLA-DR2 mice. FIG. 7A is a digital image of normal optic nerve, showing compact myelin staining. FIG. 7B is a series of digital images of longitudinal sections of optic nerves from vehicle-treated mice at days 16, 30, and 62 PI. FIG. 7C is a series of digital images of longitudinal sections of optic nerves from RTL342M-treated mice at days 16, 30, and 62 PI. FIG. 7D is a bar graph showing quantification of the intensity of myelin staining and adjusted to 0.1 mm$^2$. Values are expressed as mean±SEM of staining intensity from four optic nerves per group.

FIG. 8A-H is a series of panels showing demyelination and axonal degeneration in MOG-induced ON in HLA-DR2 transgenic mice at day 16 PI (peak). The panels are representative sequential sections of the same optic nerve with ON. FIG. 8A is a digital image showing myelin staining with H&E. FIG. 8B is a digital image showing macrophages (mφ)/microglia immunofluorescent staining with anti-CD11b antibodies (red). FIG. 8C is a digital image of myelin staining with Luxol fast blue with cresyl blue to label cells. FIG. 8D is a digital image of immunofluorescent axonal labeling using RT97 antibodies (green). Arrows show an inflammatory lesion. FIGS. 8E-H show digital images of optic nerves with Bielschowsky silver impregnation for axonal staining. FIG. 8E is a digital image of a longitudinal section of a normal optic nerve. FIG. 8F is a digital image of a longitudinal section of an affected optic nerve. FIG. 8G is a digital image of a cross section of a normal optic nerve. FIG. 8H is a digital image of a cross section of an affected optic nerve. Arrows in FIGS. 8F and 8H indicate damaged axons.

FIGS. 9A and B are a series of panels showing oligodendrocyte immunofluorescent labeling of vehicle- and RTL342M-treated optic nerves. FIG. 9A is a series of digital images of double-immunofluorescent labeling in optic nerves collected at days 30 (top) and 62 (bottom) PI labeled with anti-MOG antibodies (red), anti-RT97 antibodies (green) and colocalization shown in yellow. White arrows indicate MOG+ myelin-producing cells. FIG. 9B is a series of digital images of double immunofluorescent staining of day 62 PI vehicle- and RTL-treated optic nerves labeled with anti-MOG antibodies (red) and anti-CD11b antibodies for labeling of mφ/microglia (green). Nuclei are labeled with DAPI (blue). Yellow arrows indicate microglia, white arrows indicate MOG+ myelin-producing cells.

FIG. 10A is a series of digital images of cross sections immunostained with anti-RT97 antibodies for axons in normal and treatment groups on day 62 PI. FIG. 10B is a graph showing quantitative analysis of fluorescence density of RT97 axonal labeling in vehicle- and RTL342M-treated optic nerves collected on days 30 and 62 PI. Values are mean±SEM of fluorescence density in four sections 30 μm apart in stained optic nerves (n=4). FIG. 10C is a pair of representative digital images of retinal whole mounts with RGCs labeled with NeuN on day 62 PI taken from vehicle- and RTL42M-treated mice. FIG. 10D is a series of digital images of double-immunofluorescence labeling in the retina with anti-NeuN as a marker for RGCs and anti-GFAP antibodies as a marker for astrocytes: anti-GFAP (red), anti-NeuN (green), nuclear labeling with DAPI (blue). The images show the ganglion cell layer of representative cross sections of eyes collected from vehicle- and RTL342M-treated mice. FIG. 10E is a graph showing quantitative analysis of immunofluorescence-labeled RGCs with NeuN antibodies in retinal cross section in vehicle- and RTL342M-treated mice collected on day 62 PI. Values are mean±SEM of fluorescent cell counts from four areas of the retina (n=4) and normalized to a 0.1 mm$^2$ area.

SEQUENCE LISTING

Figure 2A:
FIG. 2A-D is a series of digital images of immunofluorescent staining of microglia with anti-OX42 antibody in RCS rat retinas.

The nucleic and amino acid sequences provided herein and in the accompanying Sequence Listing are shown using standard letter abbreviations for nucleotide bases, and single letter code for amino acids. Only one strand of each nucleic acid sequence is shown, but the complementary strand is understood as included by any reference to the displayed strand.

The Sequence Listing is submitted as an ASCII text file in the form of the file named Sequence_Listing.txt, which was created on Apr. 6, 2012, and is 10,262 bytes, which is incorporated by reference herein.

SEQ ID NO: 1 is the amino acid sequence of an exemplary monomeric human class II β1α1 molecule including MOG 35-55 peptide (RTL1000).

SEQ ID NO: 2 is the amino acid sequence of an exemplary IRBP 1177-1191 peptide.

SEQ ID NO: 3 is the amino acid sequence of an exemplary arrestin 291-310 peptide.

SEQ ID NO: 4 is the amino acid sequence of an exemplary phosducin 65-96 peptide.

SEQ ID NO: 5 is the amino acid sequence of an exemplary recoverin 48-52 peptide.

SEQ ID NO: 6 is the amino acid sequence of an exemplary recoverin 64-70 peptide.

SEQ ID NO: 7 is the amino acid sequence of an exemplary recoverin 62-81 peptide.

SEQ ID NO: 8 is the amino acid sequence of an exemplary recoverin 149-162 peptide.

SEQ ID NO: 9 is the amino acid sequence of an exemplary MOG 35-55 peptide.

SEQ ID NO: 10 is the amino acid sequence of an exemplary MOG 1-25 peptide.

SEQ ID NO: 11 is the amino acid sequence of an exemplary MOG 94-116 peptide.

SEQ ID NO: 12 is the amino acid sequence of an exemplary MOG 145-160 peptide.

SEQ ID NO: 13 is the amino acid sequence of an exemplary MOG 194-208 peptide.

SEQ ID NO: 14 is the amino acid sequence of an exemplary MBP 85-99 peptide.

SEQ ID NO: 15 is the amino acid sequence of an exemplary MBP 145-164 peptide.

SEQ ID NO: 16 is the amino acid sequence of an exemplary PLP 139-151 peptide.

SEQ ID NO: 17 is the amino acid sequence of an exemplary PLP 95-116 peptide.

SEQ ID NO: 18 is the amino acid sequence of an exemplary human MHC class II β1α1 molecule.

SEQ ID NO: 19 is the amino acid sequence of an exemplary mouse MHC class II β1α1 molecule.

SEQ ID NO: 20 is the amino acid sequence of an exemplary mouse MOG 35-55 peptide.

DETAILED DESCRIPTION

I. Abbreviations

AMD age-related macular degeneration
APC antigen presenting cell
AR autoimmune retinopathy
ERG electroretinogram
HLA human leukocyte antigen
INL inner nuclear layer
IRBP interphotoreceptor retinoid binding protein
MBP myelin basic protein
MHC major histocompatibility complex
MOG myelin oligodendrocyte glycoprotein
OCT optical coherence tomography
ONL outer nuclear layer
PLP proteolipid protein
RGC retinal ganglion cell layer
ROS rod outer segment
RP retinitis pigmentosa
RPE retinal pigment epithelium
RTL recombinant T cell receptor ligand

II. Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below.

All publications, patent applications, patents, and other references mentioned herein are incorporated by reference in their entirety. All GenBank Accession numbers mentioned herein are incorporated by reference in their entirety as present in GenBank on Apr. 7, 2011. In case of conflict, the present specification, including explanations of terms, will control. In addition, the materials, methods, and examples are illustrative only and not intended to be limiting.

In order to facilitate review of the various embodiments of the disclosure, the following explanations of specific terms are provided:

Antigen:

A compound, composition, or substance that can stimulate the production of antibodies or a T cell response in an animal, including compositions that are injected or absorbed into an animal. An antigen reacts with the products of specific humoral or cellular immunity, including those induced by heterologous immunogens. The term "antigen" includes all related antigenic epitopes. "Epitope" or "antigenic determinant" refers to a site on an antigen to which B and/or T cells respond. In one embodiment, T cells respond to the epitope, when the epitope is presented in conjunction with an MHC molecule. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 8 amino acids (such as about 8-50 or 8-23 amino acids) in a unique spatial conformation. Methods of determining spatial conformation of epitopes include, for example, x-ray crystallography and two-dimensional nuclear magnetic resonance.

An antigen can be a tissue-specific antigen, or a disease-specific antigen. These terms are not exclusive, as a tissue-specific antigen can also be a disease-specific antigen. A tissue-specific antigen is expressed in a limited number of tissues, such as a single tissue. A tissue-specific antigen may be expressed by more than one tissue, such as, but not limited to, an antigen that is expressed in retina or an antigen of the central or peripheral nervous system. In some examples, an antigen is a retinal antigen, including, but not limited to IRBP, arrestin, recoverin, rhodopsin, or phosducin, or an antigenic determinant thereof. In other examples, an antigen is an antigen of the central or peripheral nervous system, such as a myelin protein (for example, MOG, MBP, or PLP). A disease-specific antigen is expressed coincidentally with a disease process. Specific non-limiting examples of a disease-specific antigen are an antigen whose expression correlates with, or is predictive of, a retinal disease, such as retinal degeneration. A disease-specific antigen can be an antigen recognized by T cells or B cells.

Arrestin:

Also known as S-antigen, arrestin 1, rod photoreceptor arrestin (e.g., GenBank Gene ID No: 6295). Arrestin is a major soluble photoreceptor protein that is involved in desensitization of the photoactivated transduction cascade. It is expressed in the retina and the pineal gland and inhibits coupling of rhodopsin to transducin. Mutations in the arrestin gene have been associated with Oguchi disease, a rare autosomal recessive form of night blindness.

Nucleic acid and protein sequences for arrestin are publicly available. For example, GenBank Accession No. NM_000541 discloses an exemplary human arrestin nucleic acid sequence and GenBank Accession No. NP_000532 discloses an exemplary human arrestin protein sequence. Each of these sequences are incorporated by reference as provided by GenBank on Apr. 7, 2011. In some examples, an antigenic determinant of arrestin includes a portion of an arrestin protein which stimulates an immune response. In one example, an arrestin antigenic determinant includes or consists of amino acids 291-310 of human arrestin.

Autoimmune Retinopathy:

Damage to the retina caused by autoantibodies to retinal proteins, causing sudden and progressive loss of vision, leading to blindness. Autoimmune retinopathies include cancer-associated retinopathy (CAR), melanoma-associated retinopathy (MAR), autoimmune retinopathy (AR), and acute zonal occult outer retinopathy (AZOOR). Retinal proteins associated with autoimmune retinopathy include recoverin, carbonic anhydrase II, transducin-$\alpha$, transducin-$\beta$, $\alpha$-enolase, arrestin, aldolase, glyceraldehyde 3-phosphate dehydrogenase (GAPDH), IRBP, tubby-like protein 1 (TULP1), heat shock protein 70, and photoreceptor cell-specific nuclear receptor.

Diabetic Retinopathy:

Damage to the retina that occurs as a complication of diabetes. Diabetic retinopathy is caused by changes in the blood vessels of the retina. There are four stages: 1) mild nonproliferative retinopathy, which includes occurrence of microaneurysms; 2) moderate nonproliferative retinopathy, which includes blockage of some vessels that feed the retina; 3) severe nonproliferative retinopathy, which includes more severe vessel blockage; and 4) proliferative retinopathy, which includes growth of abnormal blood vessels on the retina and the vitreous. Damage to the retina and/or vision loss occurs when these vessel leak or hemorrhage. Macular edema may also occur, particularly during the nonproliferative stages of the condition. Diabetic retinopathy is considered a subset of vascular retinopathy.

Domain:

A discrete part of an amino acid sequence of a polypeptide or protein that can be equated with a particular function. For example, the $\alpha$ and $\beta$ polypeptides that constitute a MHC class II molecule are each recognized as having two domains, $\alpha 1$, $\alpha 2$ and $\beta 1$, $\beta 2$, respectively. Similarly, the $\alpha$ chain of MHC class I molecules is recognized as having three domains, $\alpha 1$, $\alpha 2$, and $\alpha 3$. The various domains in each of these molecules are typically joined by linking amino acid sequences. In one embodiment of the present disclosure, the entire domain sequence is included in a recombinant molecule by extending the sequence to include all or part of the linker or the adjacent domain. For example, when selecting the $\alpha 1$ domain of an MHC class II molecule, the selected sequence will generally extend from amino acid residue number 1 of the $\alpha$ chain, through the entire $\alpha 1$ domain and will include all or part of the linker sequence located at about amino acid residues 76-90 (at the carboxy terminus of the $\alpha 1$ domain, between the $\alpha 1$ and $\alpha 2$ domains). The precise number of amino acids in the various MHC molecule domains varies depending on the species of mammal, as well as between classes of genes within a species. The critical aspect for selection of a sequence for use in a recombinant molecule is the maintenance of the domain function rather than a precise structural definition based on the number of amino acids. One of skill in the art will appreciate that domain function may be maintained even if somewhat less than the entire amino acid sequence of the selected domain is utilized. For example, a number of amino acids at either the amino or carboxy termini of the $\alpha 1$ domain may be omitted without affecting domain function. Typically however, the number of amino acids omitted from either terminus of the domain sequence will be no greater than 10, and more typically no greater than 5 amino acids. The functional activity of a particular selected domain may be assessed in the context of the two-domain MHC polypeptides provided herein (e.g., the class II $\beta 1\alpha 1$ or class I $\alpha 1\alpha 2$ polypeptides) using the antigen-specific T-cell proliferation assay as described in detail below. For example, to test a particular β1 domain, the domain will be linked to a functional α1 domain so as to produce a β1α1 molecule and then tested in the described assay. A biologically active β1α1 or α1α2 polypeptide will inhibit antigen-specific T-cell proliferation by at least about 50%, thus indicating that the component domains are functional. Typically, such polypeptides will inhibit T-cell proliferation in this assay system by at least 75% and sometimes by greater than about 90%.

Interphotoreceptor Retinoid Binding Protein (IRBP):

Also known as interstitial retinol-binding protein or retinol binding protein 3, interstitial (e.g., GenBank Gene ID No: 5949). IRBP is a large glycoprotein known to bind retinoids and found primarily in the interphotoreceptor matrix of the retina between the retinal pigment epithelium and the photoreceptor cells. It is thought to transport retinoids between the retinal pigment epithelium and the photoreceptors, a critical role in the visual process. The human IRBP gene is approximately 9.5 kb in length and consists of four exons separated by three introns. The gene is transcribed by photoreceptor and retinoblastoma cells into an approximately 4.3 kilobase mRNA that is translated and processed into a glycosylated protein of about 135 kDa.

Nucleic acid and protein sequences for IRBP are publicly available. For example, GenBank Accession No. NM_002900 discloses an exemplary human IRBP nucleic acid sequence and GenBank Accession No. NP_002891 discloses an exemplary human IRBP protein sequence. In other examples, GenBank Accession No. XM_001060185 discloses an exemplary rat IRBP nucleic acid sequence and GenBank Accession No. XP_001060185 discloses an exemplary rat IRBP protein sequence. Each of these sequences are incorporated by reference as provided by GenBank on Apr. 7, 2011. In some examples, an antigenic determinant of IRBP includes a portion of an IRBP protein which stimulates an immune response. In one example, an IRBP antigenic determinant includes or consists of amino acids 1177-1191 of IRBP.

Isolated:

An "isolated" biological component (such as a nucleic acid, peptide or protein) has been substantially separated, produced apart from, or purified away from other biological components in the cell in which the component occurs, e.g., other chromosomal and extrachromosomal DNA and RNA, and proteins. Nucleic acids, peptides and proteins which have been "isolated" thus include nucleic acids and proteins purified by standard purification methods. The term also embraces nucleic acids, peptides and proteins prepared by recombinant expression in a host cell as well as chemically synthesized nucleic acids.

Linker:

An amino acid sequence that covalently links two polypeptide domains. Linker sequences may be included in the recombinant MHC polypeptides of the present disclosure to provide rotational freedom to the linked polypeptide domains and thereby to promote proper domain folding and inter- and intra-domain bonding. By way of example, in a recombinant polypeptide comprising Ag-β1-α1 (where Ag=antigen), linker sequences may be provided between the Ag and β1 domains and/or between the β1 and α1 domains.

Recombinant linker sequences, which are generally between 2 and 25 amino acids in length, are well known in the art and include, but are not limited to, the glycine(4)-serine spacer described by Chaudhary et al. (*Nature* 339:394-397, 1989).

Macular Degeneration:

A condition in which the cells of the macula (the central part of the retina) degenerate, resulting in loss of central visual acuity. The most common form of macular degeneration is age-related macular degeneration (AMD). AMD is the most common cause of irreversible loss of central vision and legal blindness in the elderly. It causes progressive damage to the macula, resulting in gradual loss of central vision. There are two forms, atrophic and neovascular macular degeneration. In atrophic degeneration (dry form), the tissues of the macula thin as photoreceptor cells disappear. There is currently no treatment for atrophic degeneration, though dietary supplements may help slow progression. In neovascular macular degeneration (wet form), abnormal blood vessels develop under the macula. These vessels may leak fluid and blood under the retina and eventually a mound of scar tissue develops under the retina. Central vision becomes washed out and loses detail, and straight lines may appear wavy. For neovascular macular degeneration there are some treatments available, including the use of medication injected directly into the eye (e.g., anti-VEGF therapy), laser therapy in combination with a targeting drug (e.g., photodynamic therapy) and brachytherapy. However, repeated treatments can cause complications leading to loss of vision.

Stargardt-like macular degeneration (STGD3) is an early onset, autosomal dominant macular degeneration. STGD3 is characterized by a progressive pathology, the loss of central vision, atrophy of the retinal pigment epithelium, and accumulation of lipofuscin, clinical features that are also characteristic of AMD.

Maculopathy:

Any pathological condition of the macula. Maculopathies include AMD and STGD3, as well as vitelliform macular dystrophy (Best disease), Malattia Leventinese (Doyne's honeycomb retinal dystrophy), diabetic maculopathy, occult macular dystrophy, and cellophane maculopathy.

MHC Class I:

MHC class I molecules are formed from two non-covalently associated proteins, the α chain and β2-microglobulin. The α chain comprises three distinct domains, α1, α2 and α3. The three-dimensional structure of the α1 and α2 domains forms the groove into which antigen fit for presentation to T-cells. The α3 domain is an Ig-fold like domain that contains a transmembrane sequence that anchors the α chain into the cell membrane of the APC. MHC class I complexes, when associated with antigen (and in the presence of appropriate co-stimulatory signals) stimulate CD8 cytotoxic T-cells, which function to kill any cell which they specifically recognize.

In some examples disclosed herein, an MHC class I α1α2 polypeptide includes the α1 and α2 domains of a MHC class I molecule in covalent linkage. In other examples, an α1α2 nucleic acid includes a recombinant nucleic acid sequence encoding an α1α2 polypeptide. The orientation of the polypeptide is such that the carboxy terminus of the α1 domain is covalently linked to the amino terminus of the α2 domain. An α1α2 polypeptide comprises less than the whole class I α chain, and usually omits most or all of the α3 domain of the α chain. Specific non-limiting examples of an α1α2 polypeptide include polypeptides wherein the carboxy terminus of the α1 domain is covalently linked to the amino terminus of the α2 domain of an HLA-A, HLA-B or HLA-C molecule. In one embodiment, the α3 domain is omitted from an α1α2 polypeptide, thus the α1α2 polypeptide does not include an α3 domain.

MHC Class II:

MHC class II molecules are formed from two non-covalently associated proteins, the α chain and the β chain. The α chain comprises α1 and α2 domains, and the β chain comprises β1 and β2 domains. The cleft into which the antigen fits is formed by the interaction of the α1 and β1 domains. The α2 and β2 domains are transmembrane Ig-fold like domains that anchor the α and β chains into the cell membrane of the APC. MHC class II complexes, when associated with antigen (and in the presence of appropriate co-stimulatory signals) stimulate CD4 T-cells. The primary functions of CD4 T-cells are to initiate the inflammatory response, to regulate other cells in the immune system, and to provide help to B cells for antibody synthesis.

In some examples disclosed herein, an MHC class II β1α1 polypeptide includes a recombinant polypeptide comprising the α1 and β1 domains of a MHC class II molecule in covalent linkage. In other examples, a β1α1 nucleic acid includes a recombinant nucleic acid sequence encoding a β1α1 polypeptide. To ensure appropriate conformation, the orientation of the polypeptide is such that the carboxy terminus of the β1 domain is covalently linked to the amino terminus of the α1 domain. In one embodiment, the polypeptide is a human β1α1 polypeptide, and includes the α1 and β1 domains for a human MHC class II molecule. One specific, non-limiting example of a human β1α1 polypeptide is a molecule wherein the carboxy terminus of the β1 domain is covalently linked to the amino terminus of the α1 domain of an HLA-DR molecule. An additional, specific non-limiting example of a human β1α1 polypeptide is a molecule wherein the carboxy terminus of the β1 domain is covalently linked to the amino terminus of the α1 domain of an HLA-DR (either A or B), an HLA-DP (A and B), or an HLA-DQ (A and B) molecule. In one embodiment, the β1α1 polypeptide does not include a β2 domain. In another embodiment, the β1α1 polypeptide does not include an α2 domain. In yet another embodiment, the β1α1 polypeptide does not include either an α2 or a β2 domain.

Myelin Basic Protein (MBP):

A myelin protein which is a major constituent of the myelin sheath of oligodendrocytes and Schwann cells in the central and peripheral nervous system, respectively. Nucleic acid and protein sequences for MBP are publicly available. For example, GenBank Accession Nos. NM_001025081, NM_001025090, NM_001025092, and NM_002385 disclose exemplary human MBP nucleic acid sequences, and GenBank Accession Nos. NP_001020252, NP_001020261, NP_001020263, and NP_002376 disclose exemplary human MBP protein sequences, all of which are incorporated by reference as provided by GenBank on Apr. 7, 2011. Similarly, GenBank Accession Nos. NM_001025251, NM_001025254, NM_001025255, NM_001025256, NM_001025258, and NM_001025259 disclose exemplary mouse MBP nucleic acid sequences, and GenBank Accession Nos. NP_001020422, NP_001020425, NP_001020426, NP_001020427, NP_001020429, and NP_001020430 disclose exemplary mouse MBP protein sequences, all of which are incorporated by reference as provided by GenBank on Apr. 7, 2011. One of skill in the art can identify additional MBP sequences from human, mouse, or other species.

Myelin Oligodendrocyte Glycoprotein (MOG):

A myelin protein which is a membrane protein expressed on the oligodendrocyte cell surface and the outermost surface of myelin sheaths. Nucleic acid and protein sequences for MOG are publicly available. For example, GenBank Accession Nos. NM_001008228, NM_001008229, NM_001170418, NM_002433, NM_206809, NM_206810, NM_206811, NM_206812, and NM_206814 disclose exemplary human MOG nucleic acid sequences, and GenBank Accession Nos. NP_001008229, NP_001008230, NP_001163889, NP_002424, NP_996532, NP_996533, NP_996534, NP_996535, and NP_996537 disclose exemplary human MOG protein sequences, all of which are incorporated by reference as provided by GenBank on Apr. 7, 2011. Similarly, GenBank Accession No. NM_010814 discloses an exemplary mouse MOG nucleic acid sequence, and GenBank Accession No. NP_034944 discloses an exemplary mouse MOG protein sequence, both of which are incorporated by reference as provided by GenBank on Apr. 7, 2011. One of skill in the art can identify additional MOG sequences from human, mouse, or other species.

Optic Neuritis:

A condition involving inflammation of the optic nerve. Symptoms of optic neuritis include sudden vision loss (for example, complete or partial vision loss), sudden blurring of vision, pain on eye movement, and loss or alteration of color vision. In most cases visual functions return to normal or near normal in a period of weeks, but optic neuritis may also advance to complete and/or permanent vision loss. Inspection of the optic nerve head may show inflammation in some cases, but in many cases, the optic nerve head appears normal. In some cases, optic neuritis is present in a subject with multiple sclerosis, and may be the presenting symptom of multiple sclerosis. Optic neuritis may also be present in a subject without multiple sclerosis. In some examples, optic neuritis may be caused by infection (such as syphilis, Lyme disease, or herpes zoster), other autoimmune disorders (such as temporal arteritis, lupus, or inflammatory bowel disease), diabetes, or drug-induced vasculitis (for example, as a result of chloramphenicol or ethambutol treatment of the subject).

Pharmaceutically Acceptable Carriers:

The pharmaceutically acceptable carriers useful in this disclosure are conventional. *Remington: The Science and Practice of Pharmacy*, The University of the Sciences in Philadelphia, Editor, Lippincott, Williams, & Wilkins, Philadelphia, Pa., 21$^{st}$ Edition (2005), describes compositions and formulations suitable for pharmaceutical delivery of the proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Phosducin:

Also known as 33 kDa phototransducing protein or G beta gamma binding protein (e.g., GenBank Gene ID: 5132). A phosphoprotein that is located in the outer and inner segments of the rod cells in the retina. Phosducin may participate in the regulation of visual phototransduction or in the integration of photoreceptor metabolism. It modulates the phototransduction cascade by interacting with the beta and gamma subunits of the retinal G-protein transducin. This gene is a potential candidate gene for retinitis pigmentosa and Usher syndrome type II. Alternatively spliced transcript variants encoding different isoforms have been identified.

Nucleic acid and protein sequences for phosducin are publicly available. For example, GenBank Accession Nos. NM_002597 and NM_022576 disclose exemplary human phosducin nucleic acid sequences and GenBank Accession Nos. NP_002588 and NP_072098 disclose exemplary human phosducin protein sequences. Each of these sequences is incorporated by reference as provided by GenBank on Apr. 7, 2011. In some examples, an antigenic determinant of phosducin includes a portion of a phosducin protein which stimulates an immune response. In one example, a phosducin antigenic determinant includes or consists of amino acids 65-96 of phosducin.

Proteolipid Protein (PLP):

A myelin protein which is the predominant myelin protein in the central nervous system. PLP is a transmembrane protein. Nucleic acid and protein sequences for PLP are publicly available. For example, GenBank Accession Nos. NM_000533, NM_001128834, and NM_199478 disclose exemplary human PLP nucleic acid sequences, and GenBank Accession Nos. NP_000524, NP_001122306, and NP_955772 disclose exemplary human PLP protein sequences, all of which are incorporated by reference as provided by GenBank on Apr. 7, 2011. Similarly, GenBank Accession No. NM_011123 discloses an exemplary mouse PLP nucleic acid sequence, and GenBank Accession No. NP_035253 discloses an exemplary mouse PLP protein sequence, both of which are incorporated by reference as provided by GenBank on Apr. 7, 2011. One of skill in the art can identify additional PLP sequences from human, mouse, or other species.

Purified:

The term purified does not require absolute purity; rather, it is intended as a relative term. Thus, for example, a purified peptide preparation is one in which the peptide or protein is more enriched than the peptide or protein is in its natural environment within a cell. Preferably, a preparation is purified such that the protein or peptide represents at least 50% of the total peptide or protein content of the preparation. In some embodiments, a purified preparation contains at least 60%, at least 70%, at least 80%, at least 85%, at least 90%, at least 95% or more of the protein or peptide.

Recombinant:

A recombinant nucleic acid or polypeptide is one that has a sequence that is not naturally occurring or has a sequence that is made by an artificial combination of two or more otherwise separated segments of sequence. This artificial combination is often accomplished by chemical synthesis or, more commonly, by the artificial manipulation of isolated segments of nucleic acids, e.g., by genetic engineering techniques.

Recoverin:

Also known as cancer associated retinopathy antigen or cancer-associated retinopathy protein (e.g., GenBank Gene ID No: 5957). A member of the recoverin family of neuronal calcium sensors. The recoverin protein includes three calcium-binding EF-hand domains and may prolong the termination of the phototransduction cascade in the retina by blocking the phosphorylation of photoactivated rhodopsin. Recoverin may be the antigen responsible for cancer-associated retinopathy.

Nucleic acid and protein sequences for recoverin are publicly available. For example, GenBank Accession No. NM_002903 discloses an exemplary human recoverin nucleic acid sequence and GenBank Accession No. NP_002894 discloses an exemplary human recoverin protein sequence. Each of these sequences is incorporated by reference as provided by GenBank on Apr. 7, 2011. In some examples, an antigenic determinant of recoverin includes a portion of a recoverin protein which stimulates an immune response. In one example, recoverin antigenic determinant includes or consists of amino acids 48-52, 64-70, 62-81 or 149-162 of recoverin.

Retinal Degeneration:

Deterioration of the retina, including progressive death of the photoreceptor cells of the retina or associated structures (such as retinal pigment epithelium). Retinal degeneration includes diseases or conditions such as retinitis pigmentosa, cone-rod dystrophy, macular degeneration (such as age-related macular degeneration and Stargardt-like macular degeneration), autoimmune retinopathies, and maculopathies.

Retinal Disorder:

A disease or disorder that affects the retina, for example, the function and/or structure of the retina, including the optic nerve (such as the optic nerve head). Retinal disorders include retinal degenerations, retinopathies, retinal detachment, and glaucoma.

Retinitis Pigmentosa (RP):

A group of inherited retinal disorders that eventually lead to partial or complete blindness, characterized by progressive loss of photoreceptor cell function. Symptoms of RP include progressive peripheral vision loss and night vision problems (nyctalopia) that can eventually lead to central vision loss. RP is caused by mutations is over 100 different genes, and is both genotypically and phenotypically heterogeneous. Approximately 30% of RP cases are caused by a mutation in the rhodopsin gene. The pathophysiology of RP predominantly includes cell death of rod photoreceptors; however, some forms affect cone photoreceptors or the retinal pigment epithelium (RPE). Typical clinical manifestations include bone spicules, optic nerve waxy pallor, atrophy of the RPE in the mid periphery of the retina, retinal arteriolar attenuation, bull's eye maculopathy, and peripheral retinal atrophy.

Rhodopsin:

Also known as opsin 2, rod pigment or opsin-2 (e.g., Gene ID No. 6010). A rod photoreceptor specific G protein-coupled receptor, which, when photoexcited, initiates the visual transduction cascade. Mutations in rhodopsin are present in about 30% of individuals with retinitis pigmentosa.

Nucleic acid and protein sequences for rhodopsin are publicly available. For example, GenBank Accession No. NM_000539 discloses an exemplary human rhodopsin nucleic acid sequence and GenBank Accession No. NP_000530 discloses an exemplary human rhodopsin protein sequence. Each of these sequences is incorporated by reference as provided by GenBank on Apr. 7, 2011. In some examples, an antigenic determinant of rhodopsin includes a portion of a rhodopsin protein which stimulates an immune response.

Subject:

Living multi-cellular vertebrate organisms, a category that includes both human and non-human mammals.

Therapeutically Effective Amount:

A dose or quantity of a specified compound sufficient to inhibit advancement, or to cause regression of a disease or disorder, or which is capable of relieving symptoms caused by the disease. The preparations disclosed herein are administered in therapeutically effective amounts. In some examples, this can be the amount or dose of a disclosed MHC molecule required to inhibit a retinal disorder, delay the development of a retinal disorder, or reduce the risk of developing a retinal disorder. In one embodiment, a therapeutically effective amount is the amount that alone, or together with one or more additional therapeutic agents (such as additional agents for treating a retinal disorder), induces the desired response, such as inhibition or treatment of the retinal disorder (such as retinitis pigmentosa, macular degeneration, or autoimmune retinopathy). In other examples, it is an amount of the compound that can treat one or more signs or symptoms associated with a retinal disorder in a subject.

In other examples, this can be the amount or dose of a disclosed MHC molecule required to inhibit optic neuritis, delay the development of optic neuritis, or reduce the risk of developing optic neuritis. In one embodiment, a therapeutically effective amount is the amount that alone, or together with one or more additional therapeutic agents (such as additional agents for treating optic neuritis), induces the desired response, such as inhibition or treatment of optic neuritis. In other examples, it is an amount of the compound that can treat one or more signs or symptoms associated with optic neuritis in a subject.

Treating a Disease:

A therapeutic intervention that ameliorates a sign or symptom of a disease or pathological condition, such as a retinal disorder (for example, retinal degeneration or optic neuritis). "Ameliorating" refers to a reduction in the number or severity of signs or symptoms of a disease. In some examples, treating a disease includes inhibiting the full development of the disease or condition, for example in a person who is known to have a predisposition to a disease or condition, such as a retinal disorder (for example, retinal degeneration or optic neuritis). An example of a person with a known predisposition to a retinal disorder is someone with a family history of a retinal disorder or who is known to carry a mutation associated with a retinal disorder. Inhibition of a disease can span the spectrum from partial inhibition to substantially complete inhibition (prevention) of the disease. In some examples, the term "inhibiting" refers to reducing or delaying the onset or progression of a disease. A subject to be administered with a therapeutically effective amount of a compound to inhibit or treat the disease or condition can be identified by standard diagnosing techniques for such a disorder, for example, on the basis of clinical examination, family history, or risk factor to develop the disease or disorder.

Vascular Retinopathy:

Damage to the retina that results from alterations in the blood supply to the retina. Vascular retinopathy is associated with arterial hypertension, chronic nephritis, eclampsia, diabetes, and advanced atherosclerosis. Types of vascular retinopathy include central retinal artery occlusion (for example resulting from embolism or atherosclerosis), central retinal vein occlusion (for example, resulting from trauma, thrombosis, or atherosclerosis), diabetic retinopathy (discussed above), hypertensive retinopathy (for example, resulting from chronic hypertension), and sickle cell retinopathy.

III. Overview of Several Embodiments

Disclosed herein are methods for treating a retinal disorder in a subject. Also disclosed are methods for treating optic neuritis in a subject. The disclosed methods include administering an RTL to the subject. RTLs (such as MHC class II β1α1 or MHC class I α1α2 constructs covalently linked to an antigen) are described in detail in Section IV, below.

In some embodiments, methods of treating a retinal disorder in a subject include selecting a subject with a retinal disorder and administering to the subject a therapeutically effective amount of an MHC molecule including covalently linked first, second, and third domains; wherein the first domain is an MHC class II β1 domain and the second domain is an MHC class II α1 domain, wherein the amino terminus of the α1 domain is covalently linked to the carboxy terminus of the β1 domain; or wherein the first domain is an MHC class I α1 domain and the second domain is an MHC class I α2 domain, wherein the amino terminus of the α2 domain is covalently linked to the carboxy terminus of the α1 domain; and wherein the third domain is covalently linked to the first domain and comprises a retinal antigen, thereby treating the retinal disorder in the subject. In some examples, the MHC molecule does not include an MHC class II α2 domain or an MHC class II β2 domain. In other examples, the MHC molecule does not include an MHC class I α3 domain.

In other embodiments, methods of treating optic neuritis in a subject include selecting a subject with optic neuritis and administering to the subject a therapeutically effective amount of an MHC molecule including covalently linked first, second, and third domains; wherein the first domain is an MHC class II β1 domain and the second domain is an MHC class II α1 domain, wherein the amino terminus of the α1 domain is covalently linked to the carboxy terminus of the β1 domain; or wherein the first domain is an MHC class I α1 domain and the second domain is an MHC class I α2 domain, wherein the amino terminus of the α2 domain is covalently linked to the carboxy terminus of the α1 domain; and wherein the third domain is covalently linked to the first domain and comprises an antigen of the central or peripheral nervous system, thereby treating the optic neuritis in the subject. In some examples, the MHC molecule does not include an MHC class II α2 domain or an MHC class II β2 domain. In other examples, the MHC molecule does not include an MHC class I α3 domain.

In some examples, the subject is a mammalian subject (such as a human subject or a primate or rodent subject). In some embodiments, the subject does not have uveitis. In other embodiments, the subject does not have multiple sclerosis (for example, does not have multiple sclerosis at the time of diagnosis of the retinal disorder).

In some embodiments, the disclosed methods further include measuring or assessing visual function, retinal function, and/or retinal structure of the subject, such as visual acuity, visual field, electroretinogram, Amsler grid, fundus examination, color vision, fluorescein angiography, OCT or a combination of two or more thereof. Methods of measuring visual or retinal function are known to one of skill in the art and are discussed in detail below.

The methods disclosed herein include methods for treating retinal disorders and methods for treating optic neuritis in a subject. Retinal disorders include a disease or condition that affects the retina (such as the function or structure of the retina), including the optic nerve and the RPE. In some examples, a retinal disorder includes a retinal degeneration, such as retinitis pigmentosa, cone-rod dystrophy, Leber congenital amaurosis, or a maculopathy (for example, age-related macular degeneration, Stargardt-like macular degeneration, vitelliform macular dystrophy (Best disease), Malattia Leventinese (Doyne's honeycomb retinal dystrophy), diabetic maculopathy, autoimmune retinopathy, occult macular dystrophy, and cellophane maculopathy). In other examples, a retinal disorder includes a retinopathy, such as diabetic retinopathy, or vascular retinopathy. In still further examples, a retinal disorder includes retinal detachment or glaucoma. Retinal disorders may be progressive (for example, retinal degeneration or glaucoma) or acute (for example, retinal detachment). Optic neuritis is an inflammation of the optic nerve. Optic neuritis is generally acute and resolves over time, but can recur. One of skill in the art can diagnose a retinal disorder or optic neuritis in a subject. See, e.g., Federman et al. *Retina and Vitreous, Textbook of Ophthalmology*, Vol. 9, Mosby-Yearbook, Europe, Ltd., 1994; Kanski, *Clinical Ophthalmology, A Systematic Approach*, 3$^{rd}$ Edition, Butterworth-Heinemann, Ltd., 1994.

Methods for measuring or assessing visual function, retinal function, or retinal structure in a subject are well known to one of skill in the art. See, e.g., Federman et al. *Retina and Vitreous, Textbook of Ophthalmology*, Vol. 9, Mosby-Yearbook, Europe, Ltd., 1994; Kanski, *Clinical Ophthalmology, A Systematic Approach*, 3$^{rd}$ Edition, Butterworth-Heinemann, Ltd., 1994. In some examples, methods for measuring or assessing visual function include a visual acuity test (such as using a Snellen chart, Allen picture cards, E chart, or Lebensohn chart, or ETDRS chart), color vision testing (such as Ishihara plates, Farnsworth-Munsell 100-hue test, Farnsworth D15 panel, or Lanthony desaturated test), visual field testing (such as confrontation field technique, tangent screen testing, automated perimetry device, or scanning laser ophthalmoscope), Amsler grid test, or visual sensitivity test (such as with a Goldman adaptometer) and OCT. Retinal function can be measured indirectly (for example, utilizing the visual tests described above) or directly, for example by electroretinogram (ERG), such as full-field ERG, multi-focal ERG, S-cone ERG, focal ERG, or pattern ERG. Retinal function can also be assessed utilizing the electro-oculogram (EOG). In other examples, the structure of the retina is assessed, for example, utilizing fundus examination (for example, with direct or indirect ophthalmoscope or slit-lamp), ophthalmic ultrasonography, scanning laser ophthalmoscope, or fluorescein angiography.

In some examples, treating a retinal disorder in a subject includes an increase in one or more measures of visual or retinal function (such as at least about a 20% increase, at least about a 50% increase, at least about a 75% increase, at least about an 80% increase, at least about a 90% increase, at least about a 1.5-fold increase, at least about a 2-fold increase, at least about a 3-fold increase, or at least about a 5-fold increase) in the subject as compared to a control. In other examples, treating a retinal disorder in a subject includes an increase or decrease (such as at least about a 20% increase, at least about a 50% increase, at least about a 75% increase, at least about an 80% increase, at least about a 90% increase, at least about a 1.5-fold increase, at least about a 2-fold increase, at least about a 3-fold increase, or at least about a 5-fold increase or at least about a 20% decrease, at least about a 50% decrease, at least about a 75% decrease, at least about an 80% decrease, or at least about a 90% decrease) in one or more measures of retinal structure (e.g., retinal thickness or number or size of lesions) in a subject as compared to a control. In further examples, treating optic neuritis in a subject includes an increase in one or more measures of visual or retinal function (such as at least about a 20% increase, at least about a 50% increase, at least about a 75% increase, at least about an 80% increase, at least about a 90% increase, at least about a 1.5-fold increase, at least about a 2-fold increase, at least about a 3-fold increase, or at least about a 5-fold increase) in the subject as compared to a control.

The control can be any suitable control against which to compare visual function, retinal function, or retinal structure of a subject. In some embodiments, the control is a reference value or ranges of values. For example, the reference value can be derived from the average values obtained from a group of normal control subjects (for example, subjects without a retinal disorder or optic neuritis). In further examples, the reference value is derived from the average values obtained from a group of subjects with a retinal disorder or optic neuritis (such as the same or a different retinal disorder as the subject), for example, an untreated subject or a subject treated with vehicle alone. In other examples, the control is obtained from the same subject, for example, a subject with retinal disease or optic neuritis prior to treatment.

IV. RTLs

The disclosed methods utilize RTLs in methods of treatment of a retinal disorder or optic neuritis. RTLs are monomeric recombinant polypeptides that can mimic MHC function and include only those MHC domains that define an antigen binding cleft. The RTLs are capable of antigen-specific T-cell binding and include, in the case of human class II MHC molecules, only the α1 and β1 domains in covalent linkage (and in some examples in association with an antigenic determinant). For convenience, such MHC class II polypeptides are hereinafter referred to as "β1α1." Equivalent molecules derived from human MHC class I molecules are also provided herein. Such molecules comprise the α1 and α2 domains of class I molecules in covalent linkage (and in some examples in association with an antigenic determinant). Such MHC class I polypeptides are referred to as "α1α2." These two domain molecules may be readily produced by recombinant expression in prokaryotic or eukaryotic cells, and readily purified in large quantities. Moreover, these molecules may easily be loaded with any desired peptide antigen, making production of a repertoire of MHC molecules with different T-cell specificities a simple task.

A. Recombinant MHC Class II β1α1 Molecules

The amino acid sequences of mammalian MHC class II α and β chain proteins, as well as nucleic acids encoding these proteins, are well known in the art and available from numerous sources including GenBank. Exemplary sequences are provided in Auffray et al. (*Nature* 308:327-333, 1984) (human HLA DQ α); Larhammar et al. (*Proc. Natl. Acad. Sci. USA* 80:7313-7317, 1983) (human HLA DQ β); Das et al. (*Proc. Natl. Acad. Sci. USA* 80:3543-3547, 1983) (human HLA DR α); Tonnelle et al. (*EMBO J.* 4:2839-2847, 1985) (human HLA DR β); Lawrance et al. (*Nucl. Acids Res.* 13:7515-7528, 1985) (human HLA DP α); Kelly and Trowsdale (*Nucl. Acids Res.* 13:1607-1621, 1985) (human HLA DP β); Syha et al. (*Nucl. Acids Res.* 17:3985, 1989) (rat RT1.B α); Syha-Jedelhauser et al. (*Biochim. Biophys. Acta* 1089:414-416, 1991) (rat RT1.B β); Benoist et al. (*Proc. Natl. Acad. Sci. USA* 80:534-538, 1983) (mouse I-A α); Estess et al. (*Proc. Natl. Acad. Sci. USA* 83:3594-3598, 1986) (mouse I-A β), all of which are incorporated by reference herein. In one embodiment, the MHC class II protein is a human MHC class II protein (such as HLA-DR, HLA-DQ, or HLA-DP). In a particular embodiment, the MHC class II protein is a human HLA-DR, such as HLA-DR2.

The recombinant MHC class II molecules of the present disclosure include the β1 domain of the MHC class II β chain covalently linked to the α1 domain of the MHC class II α chain. The α1 and β1 domains are well defined in mammalian MHC class II proteins. In some examples, MHC class II α chains include a leader sequence that is involved in trafficking the polypeptide and is proteolytically removed to produce the mature α polypeptide. Typically, the α1 domain is regarded as comprising about residues 1-90 of the mature chain. The native peptide linker region between the α1 and α2 domains of the MHC class II protein spans from about amino acid 76 to about amino acid 93 of the mature α chain, depending on the particular α chain under consideration. Thus, an α1 domain may include about amino acid residues 1-90 of the mature α chain, but one of skill in the art will recognize that the C-terminal cut-off of this domain is not necessarily precisely defined, and, for example, might occur at any point between amino acid residues 70-100 of the α chain. In some examples, the α1 domain includes amino acids 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, or 1-100 of a mature MHC class II α domain. In other examples, an α1 domain includes about residues 20-120 (such as about residues 20-110, 24-110, 24-109, 25-100, 25-109, 26-110, 26-109, 30-120, 32-120, 32-115, 26-90, 26-85, 26-84, or other overlapping regions) of the full length MHC class II α polypeptide. In some examples, the MHC class II α1 domain does not include an N-terminal methionine; however, an N-terminal methionine can be present, for example as a result of expression in a bacterial, yeast, or mammalian system, or the N-terminal methionine may subsequently be removed. The composition of the α1 domain may also vary outside of these parameters depending on the mammalian species and the particular α chain in question. One of skill in the art will appreciate that the precise numerical parameters of the amino acid sequence are less important than the maintenance of domain function.

Similarly, the β1 domain is typically regarded as comprising about residues 1-90 of the mature β chain. The linker region between the β1 and β2 domains of the MHC class II protein spans from about amino acid 85 to about amino acid 100 of the β chain, depending on the particular β chain under consideration. Thus, the β1 protein may include about amino acid residues 1-100, but one of skill in the art will again recognize that the C-terminal cut-off of this domain is not necessarily precisely defined, and, for example, might occur at any point between amino acid residues 75-105 of the β chain. In some examples, the β1 domain includes amino acids 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, or 1-100 of a mature MHC class II β chain. In some examples, the MHC class II β1 domain does not include an N-terminal methionine; however, an N-terminal methionine can be present, for example as a result of expression in a bacterial, yeast, or mammalian system. The composition of the β1 domain may also vary outside of these parameters depending on the mammalian species and the particular β chain in question. Again, one of skill in the art will appreciate that the precise numerical parameters of the amino acid sequence are less important than the maintenance of domain function. In one embodiment, the β1α1 molecules do not include a β2 domain. In another embodiment, the β1α1 molecules do not include an α2 domain. In yet a further embodiment, the β1α1 molecules do not include either an α2 or a β2 domain. In some examples, the MHC class II β1α1 polypeptide does not include an N-terminal methionine; however, an N-terminal methionine can be present, for example as a result of expression in a bacterial, yeast, or mammalian system, or the N-terminal methionine may subsequently be removed.

Nucleic acid molecules encoding these domains may be produced by standard means, such as amplification by the polymerase chain reaction (PCR). Standard approaches for designing primers for amplifying open reading frames encoding these domains may be employed. Libraries suitable for the amplification of these domains include, for example, cDNA libraries prepared from the mammalian species in question; such libraries are available commercially, or may be prepared by standard methods. Thus, for example, constructs encoding the β1 and α1 polypeptides may be produced by PCR using four primers: primers B1 and B2 corresponding to the 5' and 3' ends of the β1 coding region, and primers A1 and A2 corresponding to the 5' and 3' ends of the α1 coding region. Following PCR amplification of the β1 and α1 domain coding regions, these amplified nucleic acid molecules may each be cloned into standard cloning vectors, or the molecules may be ligated together and then cloned into a suitable vector. To facilitate convenient cloning of the two coding regions, restriction endonuclease recognition sites may be designed into the PCR primers. For example, primers B2 and A1 may each include a suitable site such that the amplified fragments may be readily ligated together following amplification and digestion with the selected restriction enzyme. In addition, primers B1 and A2 may each include restriction sites to facilitate cloning into the polylinker site of the selected vector. Ligation of the two domain coding regions is performed such that the coding regions are operably linked, e.g., to maintain the open reading frame. Where the amplified coding regions are separately cloned, the fragments may be subsequently released from the cloning vector and gel purified, preparatory to ligation.

In certain embodiments, a peptide linker is provided between the β1 and α1 domains. Typically, this linker is between 2 and 25 amino acids in length, and serves to provide flexibility between the domains such that each domain is free to fold into its native conformation. The linker sequence may conveniently be provided by designing the PCR primers to encode the linker sequence. Thus, in the example described above, the linker sequence may be encoded by one of the B2 or A1 primers, or a combination of each of these primers.

Exemplary MHC class II β1α1 polypeptides are disclosed in U.S. Pat. No. 6,270,772 and U.S. Pat. Application Publication Nos. 2005/0142142, 2008/0267987, and 2009/0280135; each of which is incorporated by reference in their entirety. In a particular example, an MHC class II β1α1 molecule suitable for use in the disclosed methods is RTL342m. RTL342m includes covalently linked MHC class II β1 and α1 domains covalently linked to MOG 35-55 peptide. In another example, an MHC class II β1α1 molecule suitable for use in the disclosed methods is RTL1000 (SEQ ID NO: 1). RTL1000 includes covalently linked human MHC class II β1 and α1 domains covalently linked to MOG 35-55 peptide. The MOG 35-55 peptide can be replaced with one or more different antigens, such as those disclosed below. In another example, an MHC class II β1α1 molecule suitable for use in the disclosed methods is RTL220, which includes covalently linked rat MHC class II β1 and α1 domains covalently linked to IRBP 1177-1191 peptide. The IRBP 1177-1191 peptide can be replaced with one or more different antigens, such as those disclosed below.

B. Recombinant MHC Class I α1α2 Molecules

The amino acid sequences of mammalian MHC class I α chain proteins, as well as nucleic acids encoding these proteins, are well known in the art and available from numerous sources including GenBank. Exemplary sequences are provided in Browning et al. (*Tissue Antigens* 45:177-187, 1995) (human HLA-A); Kato et al. (*Immunogenetics* 37:212-216, 1993) (human HLA-B); Steinle et al. (*Tissue Antigens* 39:134-137, 1992) (human HLA-C); Walter et al. (*Immunogenetics* 41:332, 1995) (rat Ia); Walter et al. (*Immunogenetics* 39:351-354, 1994) (rat Ib); Kress et al. (*Nature* 306:602-604, 1983) (mouse H-2-K); Schepart et al. (*J. Immunol.* 136:3489-3495, 1986) (mouse H-2-D); and Moore et al. (*Science* 215: 679-682, 1982) (mouse H-2-1), which are incorporated by reference herein. In one embodiment, the MHC class I protein is a human MHC class I protein. In a particular embodiment, the MHC class I protein is a human HLA-C.

The recombinant MHC class I molecules of the present disclosure comprise the α1 domain of the MHC class I α chain covalently linked to the α2 domain of the MHC class I chain. These two domains are well defined in mammalian MHC class I proteins. Typically, the α1 domain is regarded as comprising about residues 1-90 of the mature chain and the α2 chain as comprising about amino acid residues 90-180, although again, the cut-off points are not precisely defined and will vary between different MHC class I molecules. The boundary between the α2 and α3 domains of the MHC class I α protein typically occurs in the region of amino acids 179-183 of the mature chain. The composition of the α1 and α2 domains may also vary outside of these parameters depending on the mammalian species and the particular α chain in question. One of skill in the art will appreciate that the precise numerical parameters of the amino acid sequence are less important than the maintenance of domain function. In one embodiment, the α1α2 molecule does not include an α3 domain.

The α1α2 construct may be most conveniently constructed by amplifying the reading frame encoding the dual-domain (α1 and α2) region between amino acid number 1 and amino acids 179-183, although one of skill in the art will appreciate that some variation in these end-points is possible. Such a molecule includes the native linker region between the α1 and α2 domains, but if desired that linker region may be removed and replaced with a synthetic linker peptide. The general considerations for amplifying and cloning the MHC class I α1 and α2 domains apply as discussed above in the context of the MHC class II β1 and α1 domains.

Exemplary MHC class I α1α2 polypeptides are disclosed in U.S. Pat. No. 7,265,218 and U.S. Pat. Application Publication Nos. 2005/0142142, 2008/0267987, and 2009/0280135; each of which is incorporated by reference in their entirety.

C. Modified MHC Molecules

While the foregoing discussion uses as examples naturally occurring MHC class I and class II molecules and the various domains of these molecules, one of skill in the art will appreciate that variants of these molecules and domains may be made and utilized in the same manner as described. Thus, reference herein to a domain of an MHC polypeptide or molecule (e.g., an MHC class II β1 domain) includes both naturally occurring forms of the referenced molecule, as well as molecules that are based on the amino acid sequence of the naturally occurring form, but which include one or more amino acid sequence variations. Such variant polypeptides may also be defined in the degree of amino acid sequence identity that they share with the naturally occurring molecule. Typically, MHC domain variants will share at least 80% sequence identity with the sequence of the naturally occurring MHC domain. More highly conserved variants will share at least 90% or at least 95% sequence identity with the naturally occurring sequence. Variants of MHC domain polypeptides also retain the biological activity of the naturally occurring polypeptide. For the purposes of this disclosure, that activity is conveniently assessed by incorporating the variant domain in the appropriate β1α1 or α1α2 polypeptide and determining the ability of the resulting polypeptide to inhibit antigen specific T-cell proliferation in vitro.

Methods of determining antigen-specific T-cell proliferation are well known to one of skill in the art (see, e.g., Huan et al., *J. Chem. Technol. Biotechnol.* 80:2-12, 2005). In one example, T cells and APCs are incubated with stimulation medium only, ConA, or antigen with or without supplemental IL-2 (20 Units/ml) at 37° C. in 7% $CO_2$. The cultures are incubated for three days, the last 18 hours in the presence of [$^3$H]thymidine. The cells are harvested and [$^3$H]thymidine uptake assessed (for example by liquid scintillation counting).

Variant MHC domain polypeptides include proteins that differ in amino acid sequence from the naturally occurring MHC polypeptide sequence but which retain the specified biological activity. Such proteins may be produced by manipulating the nucleotide sequence of the molecule encoding the domain, for example by site-directed mutagenesis or the polymerase chain reaction. The simplest modifications involve the substitution of one or more amino acids for amino acids having similar biochemical properties. These so-called conservative substitutions are likely to have minimal impact on the activity of the resultant protein. Table 1 shows examples of amino acids which may be substituted for an original amino acid in a protein and which are regarded as conservative substitutions.

TABLE 1

Exemplary conservative amino acid substitutions

| Original Amino Acid | Conservative Substitutions |
|---|---|
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

More substantial changes in biological function or other features may be obtained by selecting substitutions that are less conservative than those shown above, e.g., selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions which in general are expected to produce the greatest changes in protein properties will be those in which (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histadyl, is substituted for (or by) an electronegative residue, e.g., glutamyl or aspartyl; or (d) a residue having a bulky side chain, e.g., phenylalanine, is substituted for (or by) one not having a side chain, e.g., glycine. The effects of these amino acid substitutions or deletions or additions may be assessed through the use of the described T-cell proliferation assay.

At the nucleic acid level, one of skill in the art will appreciate that the naturally occurring nucleic acid sequences that encode class I and II MHC domains may be employed in the expression vectors, but that the disclosure is not limited to such sequences. Any sequence that encodes a functional MHC domain may be employed, and the nucleic acid sequence may be adapted to conform with the codon usage bias of the organism in which the sequence is to be expressed.

In some embodiments, the disclosed MHC molecules include modified MHC molecules that include one or more amino acid changes that decrease self-aggregation of native MHC polypeptides or β1α1 or α1α2 MHC molecules. Modified MHC molecules of the disclosure are rationally designed and constructed to introduce one or more amino acid changes at a solvent-exposed target site located within, or defining, a self-binding interface found in the native MHC polypeptide. The self-binding interface that is altered in the modified MHC molecule typically includes one or more amino acid residues that mediate self-aggregation of a native MHC polypeptide, or of an "unmodified" β1α1 or α1α2 MHC molecule incorporating the native MHC polypeptide. Although the self-binding interface is correlated with the primary structure of the native MHC polypeptide, this interface may only appear as an aggregation-promoting surface feature when the native polypeptide is isolated from the intact MHC complex and incorporated in the context of an "unmodified" β1α1 or α1α2 MHC molecule. In the case of exemplary MHC class II molecules described herein (e.g., comprising linked β1 and α1 domains), the native β1α1 structure only exhibits certain solvent-exposed, self-binding residues or motifs after removal of Ig-fold like β2 and α2 domains found in the intact MHC II complex. These same residues or motifs that mediate aggregation of unmodified β1α1 MHC molecules, are presumptively "buried" in a solvent-inaccessible conformation or otherwise "masked" (e.g., prevented from mediating self-association) in the native or progenitor MHC II complex (likely through association with the Ig-fold like β2 and α2 domains).

In some examples, an MHC molecule which has a reduced potential for aggregation in solution includes an "MHC component" in the form of a single chain polypeptide that includes multiple, covalently-linked MHC domain elements. These domain elements are typically selected from a) α1 and β1 domains of an MHC class II polypeptide, or portions thereof comprising an antigen (Ag)-binding groove/T-cell receptor (TCR) interface; or b) α1 and α2 domains of an MHC class I polypeptide, or portions thereof comprising an Ag-binding groove/TCR interface. The MHC component of the molecule is modified by one or more amino acid substitutions, additions, deletions, or rearrangements at a target site corresponding to a "self-binding interface" identified in a native MHC polypeptide component of an unmodified β1α1 or α1α2 MHC molecule. The modified β1α1 or α1α2 MHC molecule exhibits a markedly reduced propensity for aggregation in solution compared to aggregation exhibited by an unmodified, control β1α1 or α1α2 MHC molecule having the same fundamental MHC component structure, but incorporating the native MHC polypeptide defining the self-binding interface. Modified β1α1 or α1α2 MHC molecules with reduced potential for aggregation are described in detail in U.S. Patent Publication No. 2005/0142142, incorporated by reference herein in its entirety.

The modified MHC molecules disclosed herein yield an increased percentage of monodisperse (monomeric) molecules in solution compared to a corresponding, unmodified MHC molecule (e.g., comprising the native MHC polypeptide and bearing the unmodified, self-binding interface). In certain embodiments, the percentage of unmodified MHC molecule present as a monodisperse species in aqueous solution may be as low as 1%, more typically 5-10% or less of total MHC protein, with the balance of the unmodified MHC molecule being found in the form of higher-order aggregates. In contrast, modified MHC molecules disclosed herein yield at least 10%-20% monodisperse species in solution. In other embodiments, the percentage of monomeric species in solution will range from 25%-40%, often 50%-75%, up to 85%, 90%, 95%, or greater of the total MHC protein present, with a commensurate reduction in the percentage of aggregate MHC species compared to quantities observed for the corresponding, unmodified MHC molecules under comparable conditions.

MHC modification typically involves amino acid substitution or deletion at target sites for mutagenesis comprising a self-binding interface (including one or more amino acid residues, or a self-binding motif formed of several target residues). Within exemplary embodiments directed toward production of modified MHC molecule that include MHC class II β1α1 components, targeted residues for modification typically include hydrophobic residues or motifs, for example valine, leucine, isoleucine, alanine, phenylalanine, tyrosine, and tryptophan. These and other target residues may be substituted for any non-hydrophobic amino acid. Suitable amino acids for generating desired MHC molecule modifications can include amino acids having aliphatic-hydroxyl side chains, such as serine and threonine; amino acids having amide-containing side chains, such as asparagine and glutamine; amino acids having aromatic side chains, such as phenylalanine, tyrosine, and tryptophan; and amino acids having basic side chains, such as lysine, arginine, and histidine.

In some examples, surface modification of an MHC molecule comprising an MHC class II component to yield much less aggregation prone form can be achieved, for example, by replacement of one or more hydrophobic residues identified in the β-sheet platform of the MHC component with non-hydrophobic residues, for example polar or charged residues. FIGS. 1A-C depict an exemplary HLA-DR2 polypeptide, an exemplary β1α1 molecule, and hydrophobic β-sheet platform residues that may be targeted for modification, respectively. In some examples, one or more hydrophobic amino acids of a central core portion of the β-sheet platform are modified, such as one or more of V102, I104, A106, F108, and L110 of a human MHC class II β1α1 RTL (for example, SEQ ID NO: 18). In some examples, hydrophobic amino acids of a central core portion of the β-sheet platform include one or more amino acids at positions 6, 8, 10, 12, and 14 of an MHC class II α chain polypeptide or α1 domain (such as a human MHC class II α polypeptide). In one example the amino acids include one or more of V6, I8, A10, F12, and L14 of a human MHC class II α chain, such as a human DRA polypeptide. One of skill in the art can identify corresponding amino acids in other MHC class II molecules or β1α1 molecules. An exemplary modified MHC class II β1α1 RTL including substitution of aspartate residues for the hydrophobic amino acids corresponding to V102, I104, A106, F108, and L110 is RTL1000 (SEQ ID NO: 1).

In particular examples, one or more of the identified hydrophobic β-sheet platform amino acids is changed to either to a polar (for example, serine) or charged (for example, aspartic acid) residue. In some examples all five of V102, I104, A106, F108, and L110 (or corresponding amino acids in another MHC molecule) are changed to a polar or charged residue. In one example, each of V102, I104, A106, F108, and L110 are changed to an aspartic acid residue.

In other examples, additional hydrophobic target residues are available for modification to alter self-binding characteristics of the β-sheet platform portion of class II MHC molecules incorporated in MHC molecules. In reference to FIG. 1C, the left arm of the diagrammed β-sheet platform includes a separate "motif" of three noted hydrophobic residues (top to bottom), L141, V138, and A133 of a human MHC class II β1α1 RTL (for example, SEQ ID NO: 18) that can be modified to a non-hydrophobic (e.g., polar, or charged) residue. Also in reference to FIG. 1C, several target hydrophobic residues are marked to the right of the core β-sheet motif, including L9, F19, L28, F32, V45, and V51 of a human MHC class II β1α1 RTL (for example, SEQ ID NO: 18), which may be regarded as one or more additional, self-binding or self-associating target "motifs" for MHC molecule modification. Any one or a combination of these residues may be targeted for modification to a non-hydrophobic residue, increasing monomeric MHC molecules.

D. Expression and Purification of Recombinant MHC Molecules

In some embodiments, the MHC molecules disclosed herein (such as MHC class II β1α1 molecules or MHC class I α1α2 molecules) are expressed in prokaryotic or eukaryotic cells from a nucleic acid construct. In their most basic form, nucleic acids encoding the MHC polypeptides of the disclosure comprise first and second regions, having a structure A-B (or B-A) wherein, for class I molecules, region A encodes the class I α1 domain and region B encodes the class I α2 domain. For class II molecules, A encodes the class II α1 domain and B encodes the class II β1 domain. Where a linker sequence is included, the nucleic acid may be represented as B-L2-A, wherein L2 is a nucleic acid sequence encoding the linker peptide. Where an antigenic peptide is covalently linked to the MHC polypeptide, the nucleic acid molecule encoding this complex may be represented as P-B-A. A second linker sequence may be provided between the antigenic protein and the region B polypeptide, such that the coding sequence is represented as P-L2-B-L1-A. In all instances, the various nucleic acid sequences that comprise the MHC polypeptide (e.g., L1, L2, B, A and P) are operably linked such that the elements are situated in a single reading frame.

Nucleic acid constructs expressing these MHC polypeptides may also include regulatory elements such as promoters (Pr), enhancers, and 3' regulatory regions, the selection of which will be determined based upon the type of cell in which the protein is to be expressed. When a promoter sequence is operably linked to the open reading frame, the sequence may be represented as Pr-B-A, or (if an antigen-coding region is included) Pr-P-B-A, wherein Pr represents the promoter sequence. The promoter sequence is operably linked to the P or B components of these sequences, and the B-A or P-B-A sequences comprise a single open reading frame. The constructs are introduced into a vector suitable for expressing the MHC polypeptide in the selected cell type.

Numerous prokaryotic and eukaryotic systems are known for the expression and purification of polypeptides. For example, heterologous polypeptides can be produced in prokaryotic cells by placing a strong, regulated promoter and an efficient ribosome binding site upstream of the polypeptide-encoding construct. Suitable promoter sequences include the beta-lactamase, tryptophan (trp), phage T7 and lambda $P_L$ promoters. Methods and plasmid vectors for producing heterologous proteins in bacteria or mammalian cells are described in Sambrook et al., *Molecular Cloning: A Laboratory Manual,* 2d ed., Cold Spring Harbor Laboratory Press, 1989; Sambrook et al., *Molecular Cloning: A Laboratory Manual,* 3d ed., Cold Spring Harbor Press, 2001; Ausubel et al., *Current Protocols in Molecular Biology*, Greene Publishing Associates, 1992 (and Supplements to 2000); and Ausubel et al., *Short Protocols in Molecular Biology: A Compendium of Methods from Current Protocols in Molecular Biology,* 4th ed., Wiley & Sons, 1999.

Suitable prokaryotic cells for expression of large amounts of fusion proteins include *Escherichia coli* and *Bacillus subtilis*. Often, proteins expressed at high levels are found in insoluble inclusion bodies; methods for extracting proteins from these aggregates are described for example, by Sambrook et al. (2001, see chapter 15). Recombinant expression of MHC polypeptides in prokaryotic cells may alternatively be conveniently obtained using commercial systems designed for optimal expression and purification of fusion proteins. Such fusion proteins typically include a protein tag that facilitates purification. Examples of such systems include: the pMAL protein fusion and purification system (New England Biolabs, Inc., Beverly, Mass.); the GST gene fusion system (Amersham Pharmacia Biotech, Inc., Piscataway, N.J.); and the pTrcHis expression vector system (Invitrogen, Carlsbad, Calif.). For example, the pMAL expression system utilizes a vector that adds a maltose binding protein to the expressed protein. The fusion protein is expressed in *E. coli*. and the fusion protein is purified from a crude cell extract using an amylose column. If necessary, the maltose binding protein domain can be cleaved from the fusion protein by treatment with a suitable protease, such as Factor Xa. The maltose binding fragment can then be removed from the preparation by passage over a second amylose column.

The MHC polypeptides can also be expressed in eukaryotic expression systems, including *Pichia pastoris, Drosophila*, Baculovirus and Sindbis expression systems produced by Invitrogen (Carlsbad, Calif.). Eukaryotic cells such as Chinese Hamster ovary (CHO), monkey kidney (COS), HeLa, *Spodoptera frugiperda*, and *Saccharomyces cerevisiae* may also be used to express the MHC polypeptides. Regulatory regions suitable for use in these cells include, for mammalian cells, viral promoters such as those from CMV, adenovirus or SV40, and for yeast cells, the promoter for 3-phosphoglycerate kinase or alcohol dehydrogenase.

The transfer of DNA into eukaryotic, in particular human or other mammalian cells, is routine. The vectors are introduced into the recipient cells as pure DNA (transfection) by, for example, precipitation with calcium phosphate or strontium phosphate, electroporation, lipofection, DEAE dextran, microinjection, protoplast fusion, or microprojectile guns. Alternatively, the nucleic acid molecules can be introduced by infection with virus vectors. Systems are developed that use, for example, retroviruses, adenoviruses, or Herpes virus.

An MHC polypeptide produced in mammalian cells may be extracted following release of the protein into the supernatant and may be purified using an immunoaffinity column prepared using anti-MHC antibodies. Alternatively, the MHC polypeptide may be expressed as a chimeric protein with, for example, β-globin. Antibody to β-globin is thereafter used to purify the chimeric protein. Corresponding protease cleavage sites engineered between the β-globin gene and the nucleic acid sequence encoding the MHC polypeptide are then used to separate the two polypeptide fragments from one another after translation. One useful expression vector for generating β-globin chimeric proteins is pSG5 (Stratagene, La Jolla, Calif.).

Expression of the MHC polypeptides in prokaryotic cells will result in polypeptides that are not glycosylated. Glycosylation of the polypeptides at naturally occurring glycosylation target sites may be achieved by expression of the polypeptides in suitable eukaryotic expression systems, such as mammalian cells.

Purification of the expressed protein is generally performed in a basic solution (typically around pH 10) containing 6M urea. Folding of the purified protein is then achieved by dialysis against a buffered solution at neutral pH (typically phosphate buffered saline at around pH 7.4).

E. Antigens

The disclosed methods utilize MHC molecules including a covalently linked retinal antigen or antigen of the central or peripheral nervous system. As is well known in the art (see for example U.S. Pat. No. 5,468,481) the presentation of antigen in MHC complexes on the surface of APCs generally does not involve a whole antigenic peptide. Rather, a peptide located in the groove between the β1 and α1 domains (in the case of MHC II) or the α1 and α2 domains (in the case of MHC I) is typically a small fragment of the whole antigenic peptide. As discussed in Janeway & Travers (*Immunobiology: The Immune System in Health and Disease,* 1997), peptides located in the peptide groove of MHC class I molecules are constrained by the size of the binding pocket and are typically 8-15 amino acids long (such as 8, 9, 10, 11, 12, 13, 14, or 15 amino acids), more typically 8-10 amino acids in length (but see Collins et al., *Nature* 371:626-629, 1994 for possible exceptions). In contrast, peptides located in the peptide groove of MHC class II molecules are not constrained in this way and are often larger, typically at least 3-50 amino acids in length (such as 8-30, 10-25, or 15-23 amino acids in length). In some examples, the peptide located in the peptide groove of an MHC class II molecule is about 15-23 amino acids in length. Peptide fragments for loading into MHC molecules can be prepared by standard means, such as use of synthetic peptide synthesis machines.

In some examples, (e.g., treating a retinal disorder, such as retinal degeneration or retinopathy), the disclosed antigens include a retinal antigen (such as IRBP, arrestin, recoverin, rhodopsin, phosducin) or an antigenic determinant thereof. In one example, the antigen includes or consists of IRBP 1177-1191 (ADGSSWEGVGVVPDV; SEQ ID NO: 2). In another example, the antigen includes or consists of arrestin 291-310 (NRERRGIALDGKIKHEDTNL; SEQ ID NO: 3). In a further example, the antigen includes or consists of phosducin 65-96 (KERMSRKMSIQEYELI HQDKEDEGCL RKYRRQ; SEQ ID NO: 4). In other examples, the antigen includes or consists of recoverin 48-52 (QFQSI; SEQ ID NO: 5), recoverin 64-70 (KAYAQHV; SEQ ID NO: 6), recoverin 62-81 (PKAYAQHVFRSFDANSDGTL; SEQ ID NO: 7), or recoverin 149-162 (EKRAEKIWASFGKK; SEQ ID NO: 8). Retinal antigens such as these may also be useful in MHC molecules for treating optic neuritis.

In some examples (e.g., treating optic neuritis), the disclosed antigens include a myelin protein (for example, myelin oligodendrocyte glycoprotein (MOG), myelin basic protein (MBP), or proteolipid protein (PLP)), or an antigenic determinant thereof. Particular antigens include or consist of MOG 35-55 (MEVGWYRPPFSRVVHLYRNGK; SEQ ID NO: 9 or MEVGWYRSPFSRVVHLYRNGK; SEQ ID NO: 20), MOG 1-25 (GQFRVIGPRHPIRALVGDEV; SEQ ID NO: 10), MOG 94-116 (GGFTCFFRDHSYQEEAAMELKVE; SEQ ID NO: 11), MOG 145-160 (VFLCLQYRLRGKL-RAE; SEQ ID NO: 12), MOG 194-208 (LVALIICYNWL-HRRL; SEQ ID NO: 13), MBP 85-99 (ENPVVH-FFKNIVTPR; SEQ ID NO: 14), MBP 145-164 (VDAQGTLSKIFKLGGRDSRS; SEQ ID NO: 15), PLP 139-151 (CHCLGKWLGHPDKFVG; SEQ ID NO: 16), and PLP 95-116 (GAVRQIFGDYKTTICGKGLSAT; SEQ ID NO: 17). Myelin protein antigens may also be useful in MHC molecules for treating other retinal disorders, such as retinal degeneration.

In some examples, the antigen is covalently linked to the MHC class II or MHC class I molecule by operably linking a nucleic acid sequence encoding the selected antigen to the 5' end of the construct encoding the MHC protein such that, in the expressed peptide, the antigenic peptide domain is linked to the amino-terminus of β1 (in the case of β1α1 molecules) or α1 (in the case of α1α2 molecules). One convenient way of obtaining this result is to incorporate a sequence encoding the antigen into the PCR primers used to amplify the MHC coding regions. Typically, a sequence encoding a linker peptide sequence will be included between the molecules encoding the antigenic peptide and the MHC polypeptide. As discussed above, the purpose of such linker peptides is to provide flexibility and permit proper conformational folding of the peptides. For linking antigens to the MHC polypeptide, the linker should be sufficiently long to permit the antigen to fit into the peptide groove of the MHC polypeptide. Again, this linker may be conveniently incorporated into the PCR primers. However, it is not necessary that the antigenic peptide be ligated exactly at the 5' end of the MHC coding region. For example, the antigenic coding region may be inserted within the first few (typically within the first 10) codons of the 5' end of the MHC coding sequence.

This genetic system for linkage of the antigenic peptide to the MHC molecule is particularly useful where a number of MHC molecules with differing antigenic peptides are to be produced. The described system permits the construction of an expression vector in which a unique restriction site is included at the 5' end of the MHC coding region (e.g., at the 5' end of β1 in the case of β1α1-encoding constructs and at the 5' end of α1 in the case of α1α2-encoding constructs). In conjunction with such a construct, a library of antigenic peptide-encoding sequences is made, with each antigen-coding region flanked by sites for the selected restriction enzyme. The inclusion of a particular antigen into the MHC molecule is then performed simply by (a) releasing the antigen-coding region with the selected restriction enzyme, (b) cleaving the MHC construct with the same restriction enzyme, and (c) ligating the antigen coding region into the MHC construct. In this manner, a large number of MHC-polypeptide constructs can be made and expressed in a short period of time.

In other examples, the β1α1 and α1α2 molecules are expressed and purified in an empty form (e.g., without attached antigenic peptide), and the antigen is loaded into the molecules using standard methods. Methods for loading of antigenic peptides into MHC molecules are described in, for example, U.S. Pat. No. 5,468,481, herein incorporated by reference. Such methods include simple co-incubation of the purified MHC molecule with a purified preparation of the antigen.

In some examples, the antigen is covalently linked to the MHC molecule by a disulfide bond. In some examples, the disulfide linkage is formed utilizing a naturally occurring cysteine residue in the MHC polypeptide (such as a cysteine residue in the MHC class II β1 domain or a cysteine residue in a MHC class I α1 domain). In some examples, the cysteine residue is in the MHC class II β1 domain or in the MHC class I α1 domain. In particular examples, the disulfide linkage utilizes Cys 17 and/or Cys 79 of a MHC β1α1 polypeptide (for example, SEQ ID NO: 19). One of skill in the art can identify corresponding cysteine residues in other MHC β1α1 MHC polypeptides. In other examples, the disulfide linkage is formed utilizing a non-naturally occurring cysteine residue in the MHC polypeptide, such as a cysteine residue introduced in the MHC polypeptide by mutagenesis. In further examples, the disulfide linkage is formed utilizing a naturally occurring cysteine residue in the peptide antigen. In still further examples, the disulfide linkage is formed utilizing a non-naturally occurring cysteine residue in the peptide antigen, such as a cysteine residue introduced in the peptide antigen by mutagenesis. Exemplary MHC molecules wherein the antigen is covalently linked by a disulfide bond are described in U.S. Provisional Pat. Application No. 61/380,191, filed Sep. 3, 2010, incorporated herein by reference in its entirety.

In one non-limiting example, empty β1α1 molecules (e.g., 1 mg/ml; 40 μM) may be loaded by incubation with a 10-fold molar excess of peptide (e.g., 10 mg/ml; 400 μM) at room temperature, for 24 hours or more. Thereafter, excess unbound peptide may be removed by dialysis against PBS at 4° C. for 24 hours. As is known in the art, peptide binding to β1α1 can be detected and/or quantified by silica gel thin layer chromatography (TLC) using radiolabeled peptide or by gel electrophoresis. Based on such quantification, the loading may be altered (e.g., by changing the molar excess of peptide or the time of incubation) to obtain the desired result.

V. Pharmaceutical Formulations and Modes of Administration

Pharmaceutical compositions that include one or more of the MHC polypeptides disclosed herein (such as 2, 3, 4, 5, or more MHC polypeptides) can be formulated with an appropriate solid or liquid carrier, depending upon the particular mode of administration chosen. The pharmaceutically acceptable carriers and excipients useful in this disclosure are conventional. See, e.g., *Remington: The Science and Practice of Pharmacy*, The University of the Sciences in Philadelphia, Editor, Lippincott, Williams, & Wilkins, Philadelphia, Pa., 21$^{st}$ Edition (2005). For instance, parenteral formulations usually include injectable fluids that are pharmaceutically and physiologically acceptable fluid vehicles such as water, physiological saline, other balanced salt solutions, aqueous dextrose, glycerol or the like. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, pH buffering agents, or the like, for example sodium acetate or sorbitan monolaurate. Excipients that can be included are, for instance, other proteins, such as human serum albumin or plasma preparations.

The dosage form of the pharmaceutical composition will be determined by the mode of administration chosen. For instance, in addition to injectable fluids, topical, inhalation, oral and suppository formulations can be employed. Topical preparations can include eye drops, ointments, sprays, patches and the like. Inhalation preparations can be liquid (e.g., solutions or suspensions) and include mists, sprays and the like. Oral formulations can be liquid (e.g., syrups, solutions or suspensions), or solid (e.g., powders, pills, tablets, or capsules). Suppository preparations can also be solid, gel, or in a suspension form. For solid compositions, conventional non-toxic solid carriers can include pharmaceutical grades of mannitol, lactose, starch, or magnesium stearate. Actual methods of preparing such dosage forms are known, or will be apparent, to those skilled in the art.

In some examples, the pharmaceutical composition may be administered by any means that achieve their intended purpose. Amounts and regimens for the administration of the selected MHC polypeptides will be determined by the attending clinician. Effective doses for therapeutic application will vary depending on the nature and severity of the condition to be treated, the particular MHC polypeptide selected, the age and condition of the patient, and other clinical factors. Typically, the dose range will be from about 0.1 μg/kg body weight to about 100 mg/kg body weight. Other suitable ranges include doses of from about 100 μg/kg to 10 mg/kg body weight or about 500 μg/kg to about 5 mg/kg. The dosing schedule may vary from once a week to daily depending on a number of clinical factors, such as the subject's sensitivity to the protein. Examples of dosing schedules are about 1 mg/kg administered twice a week, three times a week or daily; a dose of about 5 mg/kg twice a week, three times a week or daily; or a dose of about 10 mg/kg twice a week, three times a week or daily.

The pharmaceutical compositions that include a one or more of the disclosed MHC molecules can be formulated in unit dosage form, suitable for individual administration of precise dosages. In one specific, non-limiting example, a unit dosage can contain from about 1 ng to about 500 mg of MHC polypeptide (such as about 10 ng to 100 mg or about 10 mg to 100 mg, for example, about 60 mg). The amount of active compound(s) administered will be dependent on the subject being treated, the severity of the affliction, and the manner of administration, and is best left to the judgment of the prescribing clinician. Within these bounds, the formulation to be administered will contain a quantity of the active component(s) in amounts effective to achieve the desired effect in the subject being treated. In some examples, the MHC molecule is administered daily, weekly, bi-weekly, or monthly.

The compounds of this disclosure can be administered to humans or other animals on whose tissues they are effective in various manners such as topically, orally, intravenously, intramuscularly, intraperitoneally, intranasally, intradermally, intrathecally, subcutaneously, intraocularly, via inhalation, or via suppository. In one example, the compounds are administered to the subject subcutaneously. In another example, the compounds are administered to the subject intravenously. The particular mode of administration and the dosage regimen will be selected by the attending clinician, taking into account the particulars of the case (e.g., the subject, the disease, the disease state involved, and whether the treatment is prophylactic). Treatment can involve monthly, bi-monthly, weekly, daily or multi-daily doses of compound(s) over a period of a few days to months, or even years.

In some embodiments, the disclosed RTLs can be included in an inert matrix for either topical application or injection into the eye, such as for intravitreal administration. As one example of an inert matrix, liposomes may be prepared from dipalmitoyl phosphatidylcholine (DPPC), such as egg phosphatidylcholine (PC). Liposomes, including cationic and anionic liposomes, can be made using standard procedures as known to one skilled in the art. Liposomes including one or more RTLs can be applied topically, either in the form of drops or as an aqueous based cream, or can be injected intraocularly. In a formulation for topical application, the RTL is slowly released over time as the liposome capsule degrades due to wear and tear from the eye surface. In a formulation for intraocular injection, the liposome capsule degrades due to cellular digestion. Both of these formulations provide advantages of a slow release drug delivery system, allowing the subject to be exposed to a substantially constant concentration of the RTL over time. In one example, the RTL can be dissolved in an organic solvent such as DMSO or alcohol as previously described and contain a polyanhydride, poly(glycolic) acid, poly(lactic) acid, or polycaprolactone polymer.

The RTL can be included in a delivery system that can be implanted at various sites in the eye, depending on the size, shape and formulation of the implant, and the type of transplant procedure. The delivery system is then introduced into the eye. Suitable sites include but are not limited to the anterior chamber, anterior segment, posterior chamber, posterior segment, vitreous cavity, suprachoroidal space, subconjunctiva, episcleral, intracorneal, epicorneal and sclera. In one example, the RTL delivery system is placed in the anterior chamber of the eye. In another example, the RTL delivery system is placed in the vitreous cavity.

In some examples, a therapeutically effective amount of a disclosed MHC polypeptide can be the amount of an MHC polypeptide (such as an MHC class II β1α1 polypeptide or an MHC class I α1α2 polypeptide) including an antigen (such as a retinal antigen, for example, IRBP or arrestin) necessary to treat or inhibit a retinal disorder (such as retinal degeneration) in a subject. In other examples, a therapeutically effective amount of a disclosed MHC polypeptide can be the amount of an MHC polypeptide (such as an MHC class II β1α1 polypeptide or an MHC class I α1α2 polypeptide) including an antigen (such as a central or peripheral nervous system antigen, such as a myelin protein) necessary to treat or inhibit optic neuritis.

The present disclosure also includes combinations of one or more of the disclosed RTLs with one or more other agents useful in the treatment of a disorder of the retina or optic nerve. For example, the compounds of this disclosure can be administered in combination with effective doses of one or more therapies for retinal disorders, including but not limited to, gene therapy, vitamin or mineral supplements (such as vitamins A, C, and/or E, or zinc and/or copper), anti-angiogenic therapy (such as ranibizumab or bevacizumab), photocoagulation, photodynamic therapy, lutein or zeaxanthin, corticosteroids, or immunosuppressants. Appropriate combination therapy for a particular disease can be selected by one of skill in the art. For example, the RTLs of this disclosure can be administered in combination with an anti-angiogenic therapy, such as an anti-VEGF antibody (for example, bevacizumab or ranibizumab), an anti-VEGF nucleic acid (for example pegaptanib), or a VEGFR inhibitor (such as lapatinib, sunitinib, or sorafenib), to a subject with age-related macular degeneration. In other examples, the compounds of this disclosure can be administered in combination with effective doses of one or more therapies for optic neuritis (such as a corticosteroid, for example, methylprednisolone or prednisone). The term "administration in combination" or "co-administration" refers to both concurrent and sequential administration of the active agents.

The following examples are provided to illustrate certain particular features and/or embodiments. These examples should not be construed to limit the disclosure to the particular features or embodiments described.

EXAMPLES

Example 1

Effect of RTL in a Rat Model of Retinal Degeneration

RCS pigmented dystrophic rats show gradual retinal degeneration during the first 3 months of life associated with the progression of retinal vascular abnormalities over a 2-year period (Villegas-Perez et al., *J. Comp. Neurol.* 392:58-77, 1998; Zambarakji et al., *Exp. Eye Res.* 82:164-171, 2006). Some histopathological features observed in the RCS rat are similar to those seen in certain forms of RP, including the loss of photoreceptors, invasion of retinal pigment epithelium (RPE) cells into the inner retina, narrowing of blood vessels and thickening of the vascular basal lamina, the presence of neovascular formations, "leaky" blood vessels, and the formation of preretinal membranes (Villegas-Perez et al., *J. Comp. Neurol.* 392:58-77, 1998). In addition, these rats show the presence of autoantibodies and T cells specific to IRBP.

Methods

The major epitope of IRBP is composed of amino acid residues 1177-1191 (IRBP 1177-1191; also called R16 (Sanui et al., *J. Exp. Med.* 169:1947-1960, 1989; Sasamoto et al., *Invest. Ophthalmol. Vis. Sci.* 33:2641-2649, 1992)); this was used to design and express the rat RTL220 construct (Adamus et al., *Ophthalm. Res.* 44:24-33, 2010). The RTL220 construct is a single gene encoding a polypeptide of 220 amino acids containing the β1 and α1 domains of the rat MHC class II (RT1.B) and the IRBP 1177-1191 (ADGSS-WEGVGVVPDV; SEQ ID NO: 2) peptide covalently linked to the amino terminus of the β1 domain (U.S. Pat. Publication No. 2011/0008382, incorporated herein by reference). The plasmid sequences were confirmed as described previously (Burrows et al., *Prot. Eng.* 12:771-778, 1998). The construct was expressed in *Escherichia coli*. RTL220 was purified by chromatography following the same methodology that was used to make the "empty" RTL (RTL101; β1α1 chain only) described previously (Burrows et al., *Prot. Eng.* 12:771-778, 1998).

Rats were treated with 20-200 µg RTL220 at the onset of retinal degeneration every day or every other day subcutaneously. As a control treatment RTL101 ("empty" RTL) was used. At the end of experiment at P60 or until P90 (at this time most of outer nuclear layers (ONL) disappears and are reduced to the debris zone), eyes were removed and immersed in 4% paraformaldehyde for 1 hour and then in 30% sucrose followed by freezing in OCT. Cryosections (10 µm) were stained in crystal violet or H&E to assess histopathology and retinal lamination. The vascular leakage was assessed at P90 by fluorescein angiography by injecting the rats with FITC-dextran (50 mg/ml) i.v. 30 minutes before the end of experiment. Then, eyes were dissected and fixed in 2% paraformaldehyde for 30 minutes, followed by the preparation of retinal whole mounts. The retinas were examined in a fluorescent or confocal microscope equipped with a camera to acquire serial images of the entire retina. Single images were stitched together using Photoshop software to compose the entire retina, which allowed the progress of vascular events to be followed. To assess vascular changes the retinal whole mounts were post-fixed, washed and then immersed in 0.02% NADPH-diaphorase and 0.04% nitroblue tertrazolium in 3% Triton X-100 for 90 minutes at 37° C. on a shaker to reveal retinal vessels. The enzymatic reaction was terminated by washing in PBS and then the retinas were mounted on a glass slide, dehydrated, and coverslipped. The retinas were examined under a light microscope with a digital camera (Olympus) and a series of pictures were taken from the NADPH-diaphorase staining. Again, the images were stitched for evaluation using Photoshop software.

Results

Figure 2B:
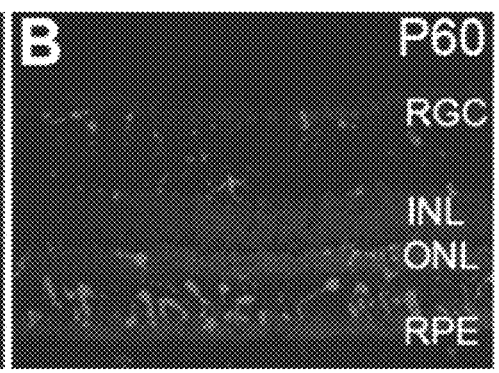
Figure 2C:
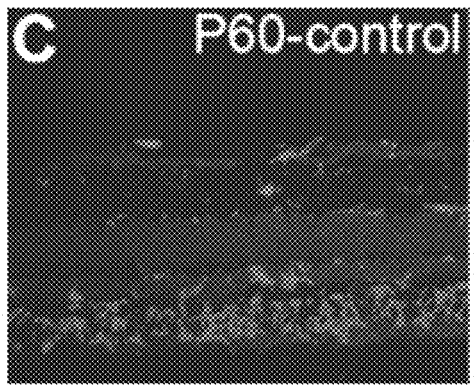
Figure 2D:
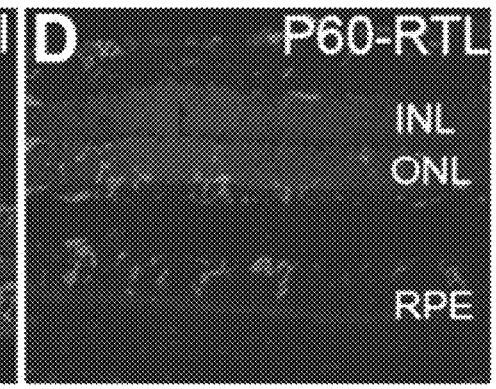

Untreated RCS rats showed considerable activation of microglia starting at day P30 and a dramatic increase at P60, associated with the reduction of photoreceptor numbers (FIGS. 2A and 2B). Initially, rats were treated with 200 µg RTL220 every other day for 10 days and once a week thereafter. These rats showed a significantly reduced number of activated microglia in the subretinal space, where the debris accumulated during degenerative progress (FIG. 2D) compared with age-matched untreated rats (FIG. 2B). Treatment with control RTL101 (empty RTL without the antigenic peptide) did not inhibit the microglia activation (FIG. 2C). Treatment with RTL220 also protected the retina from degeneration, revealing a significant survival of photoreceptors in the RTL220-treated retina (FIG. 3B), in contrast to the RTL101-treated rats where only 3-4 layers of photoreceptors remained (FIG. 3A). Also, there was a considerable reduction in the formation of vascular complexes in RTL220-treated retinas as shown in FIGS. 3C and 3D. These results indicate that RTL220 is effective in protecting the retina from photoreceptor degeneration as well as in the protection of vasculature in RCS rats.

RTL220 was also administrated daily at a dose of 20 μg/day s.c. from P30 until P90 to evaluate the effectiveness a small dose delivered when degenerative process already started. Controls consisted of the following groups: RTL101 (β1α1 no peptide), RTL201 (MBP 72-99 peptide tethered to β1α1), vehicle (saline), free IRBP 1179-1191 peptide in saline (the same peptide that is a part of RTL220), and untreated age-matched rats. One eye was collected for retinal cross-section evaluation of neuroprotective effect of RTL therapy, and the other eye for fluorescent angiography and NADPH histology of the vascular network using retinal whole mounts.

Figure 4A:
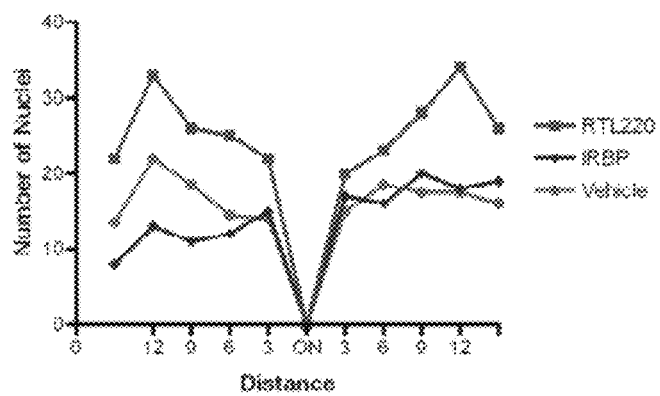
FIG. 4A is a graph showing preservation of nuclei in ONL in RTL220-treated RCS rats (RTL220) and lack of preservation of the ONL in RCS rats treated with free IRBP 1177-1191 peptide (IRBP), and vehicle treated RCS rats at P90. ON, optic nerve.
Figure 4B:
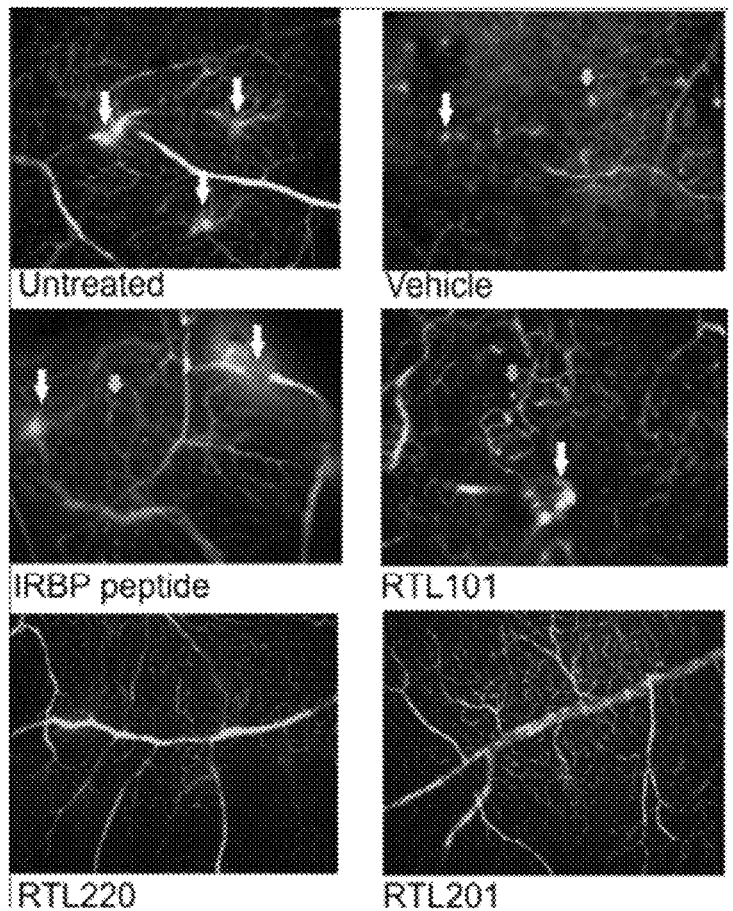
FIG. 4B is a series of digital images of fluorescein angiography of retinal whole mounts in RCS rats at P90 treated as shown. Arrows show vessel leakage.

In untreated RCS rats, the progression of degeneration resulted in complete damage of outer segments, which were reduced to 1 layer by 13 weeks (FIG. 4A). RTL220 therapy was effective in neuroprotection of the rat retina from photoreceptor degeneration as well as in the protection of vasculature in those rats. There was a substantial preservation of photoreceptors in RTL220-treated retina at P90; the number of nuclei in ONL from RT220-treated was significantly higher ($p<0.002$) than controls. Using major vessels as landmarks it was possible to provide direct correlation between fluorescent angiography and histology. Untreated and controls at P90-92 showed abnormal vascular formation associated with pigmented cells (vascular complexes) distributed mostly ventral to the optic nerve. In controls there were vascular complexes present around the optic nerve associated with vascular leakage, capillary closure and pigment migration. RTL220 significantly reduced the number of those complexes (FIG. 4B). A similar protective effect was observed with RTL201, which includes a non-retinal-specific peptide. The retinal and vascular protection with RTLs still required a peptide attached to the α1β2 polypeptide, because RTL101 was not effective.

Example 2

Analysis of Visual Function in an RTL-Treated Animal Model of Retinal Degeneration This example describes methods for analyzing the protective effect of RTLs on visual function in an animal model of retinal degeneration.

An animal model of degeneration (such as RCS rats) is treated with antigen loaded RTL (such as RTL220) or control (empty) RTL (such as RTL101), as described in Example 1. One of skill in the art can select an RTL including an appropriate antigen for the particular disease. Other animal models of retinal degeneration are well known to one of skill in the art and include, but are not limited to, mouse models, such as rd mice (rd1-10 mouse strains), vitiligo, and cone photoreceptor function loss (cpfl1) (e.g., Jackson Laboratory, jax.org), rat models, such as RCS rats and rhodopsin mutant rats, and canine models, such as the RPE65 mutant dog. There are also animal models of AMD (see, e.g., Zeiss, *Vet. Pathol.* 47:396-413, 2010). One of skill in the art can identify and select appropriate animal models for experiments such as those described in this example, as well as Examples 3 and 4.

Visual acuity of control and treated animals is assessed. The virtual optomotor system provides a simple, noninvasive, and precise method for rapidly quantifying rodent vision, including measurements of spatial frequency and contrast sensitivity thresholds of the optokinetic response (e.g., Prusky et al., *Invest. Ophthalmol. Vis. Sci.* 45:4611-4616, 2004). This is a non-invasive technique that does not require anesthesia. Subjects are standing unrestrained on a platform in the center of a square and track the grating with reflexive head movements. Acuity is obtained in each subject in less than 10 minutes, and a detailed contrast sensitivity curve is generated in approximately 30 minutes. The spatial frequency of the grating is clamped at the viewing position by repeatedly re-centering the cylinder on the head of the test subject. Acuity is quantified by increasing the spatial frequency of the grating until an optomotor response is no longer elicited. The differences that include testing at a spatial frequency begin with a grating of 100% contrast, which is reduced stepwise until the contrast threshold is identified. For normal mice, a contrast threshold is identified at six spatial frequencies between 0.03 and 3.5 cyc/deg (0.031, 0.064, 0.092, 0.103, 0.192, 0.272 cyc/deg). The threshold at a spatial frequency is calculated as a Michelson contrast from the screen's luminance (maximum−minimum)/(maximum+minimum). The contrast sensitivity (the reciprocal of the threshold) is plotted against spatial frequency on a log-log graph. Experimenters are masked to previously recorded thresholds and treatment conditions whenever possible, and thresholds are confirmed by more than one observer. At the end of experiments rodents are euthanized and eyes and optic nerves are subjected to histopathological examination such as described in Example 1. Typically, visual acuity in untreated RCS rat decreases with age from 0.5 cycle/degree (c/d) at P30 to 0.3 c/d at P90.

Visual discrimination is tested in treated and control animals (e.g., McGill et al., *Invest. Ophthalmol. Vis. Sci.* 45:932-936, 2004). The apparatus consists of a trapezoid-shaped tank containing water, with two computer monitors facing through a clear glass wall into the wide end of the pool. Visual stimuli (sine-wave gratings and gray) are generated and projected on the screens using a computer program (Vista; CerebralMechanics; available at cerebralmechanics.com). On the screens, the black level is 0.05 $cd/m^2$ and the white level is 72.8 $cd/m^2$, when measured with a light meter (model LS-110; Minolta, Osaka, Japan) positioned at the point where the animal makes a choice. This point is defined by a 46-cm midline divider that extends into the pool from between the monitors, creating a Y-maze with a stem and two arms. A moveable, transparent Plexiglas escape platform (37 cm long×13 cm wide×14 cm high) is always submerged directly below whichever monitor displays the grating. An LRLLR-LRR sequence, a pattern the animals could not memorize, is used for the location of the gratings.

Photopic and scotopic ERGs are recorded from RTL220-treated and vehicle-treated RCS rats and compared to Long Evans non-dystrophic rats. Rats are dark-adapted overnight at the beginning and end of experiments. For ERG recordings, the rats are fully anesthetized. ERGs are recorded using a microfiber electrode placed on the edge of the corneal surface. Subdermal needle electrodes serve as the reference and ground leads. The reference electrode is inserted under the skin near the ear. Light stimulus is provided by a Grass PS-22 photostimulator. The ERG is recorded and amplified signals are fed into a computer. The amplitude and implicit times of averaged ERG are measured from a printout of the digital values of the ERG. After final recordings are made, the eyes are removed and subjected to histology.

The effectiveness of treatment to improve visual function in the animal model can be demonstrated by improved visual acuity as compared to a control (such as an age-matched, untreated animal). The effectiveness of treatment can also be demonstrated by improved visual discrimination as compared to a control (such as an age-matched, untreated animal). The effectiveness of treatment can also be demonstrated by preservation, slowed deterioration, or improvement of ERG profiles.

Example 3

Analysis of Retinal Structure in RTL-Treated Animal Model

Animal models of degeneration (such as RCS rats or other animal models) are treated with antigen loaded RTL (such as RTL220) or control (empty) RTL (such as RTL101), as described in Example 1.

Following treatment with antigen loaded or control RTLs, animals are injected with fluorescein isothiocyanate (FITC)-conjugated dextran and the eyes are subjected to histological studies. After deep anesthesia with xylazine hydrochloride and ketamine hydrochloride, FITC-conjugated dextran (70 kDa, 50 mg/mL in PBS) is injected intravenously. After 30 minutes, eyes are collected. One eye is utilized for preparation of retinal whole mount for angiographic analysis and the other eye for hematoxylin and eosin staining.

For hematoxylin and eosin staining, eyes are removed and fixed in 4% paraformaldehyde for 2 hours and then in 30% sucrose overnight, and frozen in OCT compound. Frozen tissues are sectioned at 10 μm along the vertical meridian of the eye through the optic nerve head and stained with hematoxylin and eosin. The degree of retinal damage is assessed by counting the surviving photoreceptor nuclei across the retina. For the photoreceptor nuclei, the counts are begun at approximately 200 μm from the optic nerve head and are made every 400 μm for both the nasal to temporal superior and inferior hemispheres (e.g., a total of 10 measuring points). The number of photoreceptor nuclei and the thickness of the ONL are averaged for analysis.

To examine whether RTLs have a vascular protective role, retinal vessels are stained with the nicotinamide adenine dinucleotide phosphate (NADPH) diaphorase on retinal whole mount preparation. The left retina from each animal is washed in 0.1 M Tris buffer (pH 7.6) and reacted for 45 minutes in the NADPH-d reaction solution, which contains 0.25 mg/mL nitroblue tetrazolium (Sigma Chemical Co., St. Louis, Mo.), 1 mg/mL β-NADPH (Roche Molecular Biochemicals, Mannheim, Germany) and 0.5% TRITON® X-100 (Sigma) in 0.1 M Tris buffer (pH 7.6) at 37° C. Tissue is then washed in Tris buffer, mounted, and coverslipped with aqueous mounting medium (Glycergel; Dako, Carpinteria, Calif.). Control experiments are performed by omitting β-NADPH, whereupon staining fails to occur.

The effectiveness of treatment to improve or preserve retinal structure in the animal model can be demonstrated by increased retinal thickness (for example, ONL thickness, number of photoreceptor nuclei, or thickness of debris zone and ROS) as compared to a control (such as an age-matched, untreated animal). The effectiveness of treatment to improve or preserve retinal structure in the animal model can also be demonstrated by decreased vascularization or number of vascular complexes as compared to a control (such as an age-matched, untreated animal).

Example 4

Analysis of Immune Parameters in RTL-Treated Animal Model of Retinal Degeneration Animal models of degeneration (such as RCS rats) are treated with antigen loaded RTL (such as RTL220) or control (empty) RTL (such as RTL101), as described in Example 1.

The retinal tissue is dissected from eyes or treated and control animals. Tissues are stored at −80° C. before protein extraction. Cytokines are extracted from each eye with PBS by homogenization. The soluble fraction is collected by centrifugation, and then used as a cytokine source for determination. Spleen cells are cultured at $5 \times 10^5$ cells/well in a 96-well flat-bottom culture plate in RPMI stimulation medium with 20 μg/ml peptide (such as IRBP 1177-1191) for 48 hours. Supernatants are harvested and stored at −80° C. until testing for cytokines. A multiplex cytokine detection kit (Millipore, Billerica, Mass., such as a customized rat Beadlyte multiplex kit) is used to detect MCP-1, IFNγ, IL-1β, IL-4, IL6, IL-17, TNFα, IL-10, and IL-2 simultaneously according to the manufacturer's protocol. The signals are analyzed using Bio-Plex Management software (Bio-Rad, Hercules, Calif.).

Ninety-six well plates are coated with 1 μg/well antigen or "empty" RTL in 0.1 M Tris-HCl, pH9.0 and incubated overnight at room temperature. Plates are blocked with 2% BSA in PBS for 1 hour at room temperature. Then, 100 μl diluted serum sample from treated and control animals in 1% BSA in PBS is added to each well and incubated for 1 hour at room temperature. After washing, 100 μl of 1000× diluted goat anti-mouse IgG conjugated to HRP (Invitrogen, Carlsbad, Calif.) of biotinylated IgG, IgM, or IgG1/G2a is added to the wells for 1 hour incubation following the incubation with ABTS peroxidase substrate for 30 minutes to develop color reaction. The absorbance is measured at 405 nm using a BioRad plate reader (Bio-Rad, Hercules, Calif.). Significance between controls and treatment groups is determined by one-way analysis of variance ANOVA or by Mann-Whitney test.

Example 5

Treatment of Retinal Disorder with RTLs

This example describes exemplary methods for treating a retinal disorder (such as retinal degeneration) in a subject and exemplary methods for assessing efficacy of RTLs for treating a retinal disorder in a subject. However, one of skill in the art will appreciate that methods that deviate from these specific methods can also be used to treat a retinal disorder in a subject.

Subjects having a retinal disorder (such as RP, AMD, or AR) are selected. Subjects are treated weekly (for example, by subcutaneous injection) with an RTL (for example for 1, 2, 4, 8, 12, 18, 24, or more weeks), for example, an MHC class II β1α1 polypeptide covalently linked to a retinal antigen (such as IRBP, for example, IRBP 1177-1191) or other RTLs as disclosed herein, at doses of 0.1 mg/kg to 10 mg/kg. Subjects are assessed for measures of visual or retinal function (such as visual acuity, visual field, electroretinogram, OCT, Amsler grid, fundus examination, color vision test, or fluorescein angiography), prior to initiation of therapy, periodically during the period of therapy, and/or at the end of the course of treatment.

The effectiveness of RTL therapy to treat or inhibit a retinal disorder in a subject can be demonstrated by an improvement in one or more measures of visual or retinal function or a decrease in progression of one or more symptoms of the retinal disorder, for example, compared to a control, such as an untreated subject, a subject with retinal disorder prior to treatment (for example, the same subject prior to treatment), or a subject with retinal disorder treated with placebo (e.g., vehicle only).

Example 6

Effect of RTL in a Mouse Model of Optic Neuritis

Methods

Animals:

Inbred HLA-DR2 (DRA:DRβ1*1501) transgenic mice 8 to 10 weeks old were utilized in these experiments.

Recombinant T-Cell Receptor Ligand:

HLA-DR2 (DRA:DRβ1*1501)-derived RTL covalently linked to the encephalitogenic mouse MOG 35-55 peptide (MEVGWYRSPFSRVVHLYRNGK; SEQ ID NO: 20) was produced as previously described (Burrows et al., *Curr. Drug Targets Inflamm. Allergy* 4:185, 2005; Link et al., *Clin. Immunol.* 123:95-104, 2007; Vandenbark et al., *J. Immunol.* 171: 127-133, 2003). RTL342M comprises the β1 and 1 domains of DR2 (DRβ1*1501; DRA*0101) covalently linked to the MOG 35-55 peptide.

Induction and Assessment of ON:

To induce EAE and ON, groups of seven 8-12-week-old male and female transgenic mice expressing the DR2 allele were immunized with 200 μm MOG35-55 peptide in CFA containing 400 μg *Mycobacterium tuberculosis* H37RA subcutaneously (SC) at four sites on the flanks. (Rich et al., *Eur. J. Immunol.* 34:1251-1261, 2004; Vandenbark et al., *J. immunol.* 171:127-133, 2003). In addition, the mice received 70 ng pertussis toxin on days 0 and 2 post-immunization (PI). At the onset of ON, the mice were given five daily 20 μg SC doses of RTL342M. Control mice received five doses of buffer vehicle (Tris buffer) at the same times. The mice were assessed daily for clinical signs of EAE as previously published (Sinha et al., *J. Neurosci.* 27:12531-12539, 2007). At the end of the experiment, each mouse was perfused with 4% PFA, and the eyes with optic nerves and full vertebral column were dissected and fixed for 2 hours. The tissues were transferred to 30% sucrose for overnight incubation at 4° C. Next, the spinal cords were dissected from bone column, and all tissues were frozen in OCT and stored at −80° C. until sectioning. Optic nerve cryosections were cut in 10 μm longitudinal (left eyes) and cross sections (right eyes). Spinal cords were cut in 10 μm cross sections only. The optic nerve sections were stained with hematoxylin/eosin (H&E) and evaluated for the presence of inflammatory cell infiltration in longitudinal sections of the optic nerve, according to a scale from 0 to 4 by a masked observer: 0, no infiltration; 1, mild cellular infiltration of the optic nerve or optic nerve sheath; 2, moderate infiltration; 3, severe infiltration; and 4, massive infiltration of the optic nerve parenchyma and nodule infiltration. Intraocular cellular infiltration was not observed in any of the mouse eyes.

Myelin Quantification:

Frozen longitudinal sections of optic nerves from each treatment group were stained with Luxol fast blue without cresyl violet, to stain myelin only. Micrographs were then taken at 20× magnification of each section with a light microscope (model BH-2; Olympus, Tokyo, Japan) with an attached camera (DP21; Olympus) and were cropped to 0.119×0.506 mm. The cropped images were then pixilated by the ImageJ program with the Hessian plug-in feature, as described by Grider et al., *J. Neurosci. Meth.* 155:172-179, 2006 (ImageJ, developed by Wayne Rasband, National Institutes of Health, Bethesda, Md.; available at rsb.info.nih.gov/ij/index.html). Pixilation intensity was counted from the whole assigned area in a masked fashion using Image ProPlus and graphed (Prism; GraphPad, San Diego, Calif.). The area was normalized to 0.1 mm$^2$.

Immunofluorescent Staining:

Frozen long or cross sections were postfixed with 4% paraformaldehyde in PBS for 10 minutes, washed, and blocked with 10% normal goat serum in PBS containing 1% BSA and 0.2% Tween for 1 hour. After the primary antibodies were blocked in PBS with 1% BSA and 0.2% Tween, the sections were incubated for 1 hour at room temperature. The following antibodies were used: anti-MOG (1:200; Abnova, Walnut, Calif.), anti-CD11b (1:100; Abcam, Cambridge, Mass.), anti-RT97 (1:500; Millipore, Billerica, Mass.), anti-MBP (1:200; Abnova), anti-NeuN (1:100; Chemicon, Temecula, Calif.), and anti-GFAP (1:100; BD Pharmingen, San Diego, Calif.) for overnight incubation at 4° C. Next, tissue was washed and incubated in appropriate secondary antibodies in PBS with 1% BSA, 0.2% Tween for 1 hour, including anti-mouse AlexaFluor 488 (1:400), anti-rabbit AlexaFluor 594 (1:400), or anti-goat AlexaFluor 594 (1:400; all from Invitrogen, Carlsbad, Calif.). After the tissues were washed, DAPI (Roche, Indianapolis, Ind.) counterstain was applied for 1 minute, and the slides were then mounted (Fluoromount-G; Southern Biotech, Birmingham, Ala.) to be photographed with a confocal fluorescence microscope (Fluoview 1000; Olympus, or DM5000 Leica, Deerfield, Ill.). Pictures were then taken at 10× and 20× magnifications and analyzed (ImagePro; Media Cybernetics, Silver Spring, Md.). A negative control contained secondary antibodies only.

Axon Quantification:

Ten-micrometer cross sections of experimental and age-matched normal optic nerves were prepared every 30 μm for immunostaining with anti-RT97 antibodies. At least four sections were used from each animal. Anti-RT97 (Millipore) diluted at 1:500 were used for 1 hour followed by incubation with anti-mouse Alexa Fluor 488 diluted at 1:400 for another hour and then counterstain with DAPI (Roche) for mounting. Pictures were taken of each stained section at 40× magnification using a confocal microscope (Fluoview1000; Olympus), and pseudocolor images were acquired for analysis. The images were then cropped to the same 220×130 μm area and counted in a masked fashion based on the intensity of the fluorescent green stain (ImagePro Plus; Media Cybernetics). The negative control was also stained and counted to subtract the background from all the counts.

RGC Evaluation:

Retinas were removed from fixed left eyes, and whole mounts were made by four radial cuts representing the dorsal, ventral, temporal, and nasal sides. Cross sections (10 μm) were prepared from the right eye. The retinas were placed in a solution containing 100_diluted anti-NeuN antibodies that labeled RGCs specifically, followed by fluorescent anti-mouse Alexa488 diluted 400×. After a brief wash, the retinas were flat mounted on the slide, and retinal images were captured at 10× magnification with a fluorescence microscope (DM5000B; Leica) and photographed. RGCs were counted in a masked fashion with the imaging software.

Statistical Analysis:

The data are expressed as the mean±SEM. A two-tailed Student's t-test was used to determine the statistical significance. The significance between the controls and treatment groups was determined by one-way analysis of variance (ANOVA; Prism 3.0; GraphPad). Differences with a $P<0.05$ were significant.

Results

Figure 5A:
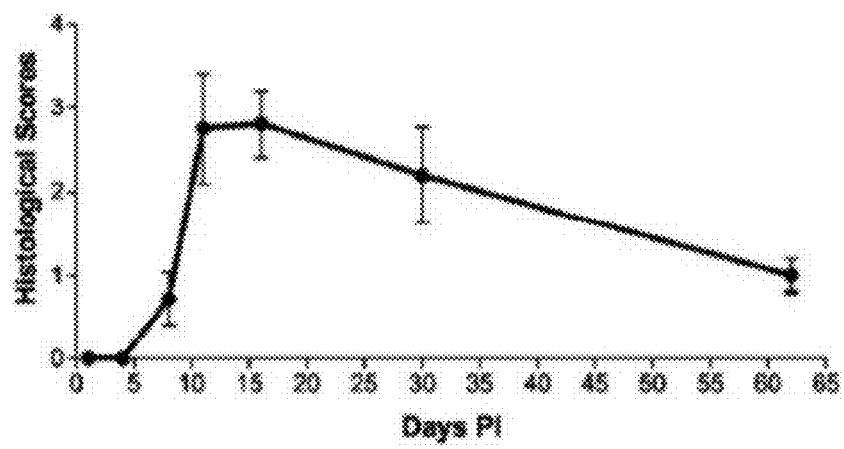
FIG. 5A-D is a series of panels showing pathology of ON associated with EAE in HLA-DR2 mice induced with MOG 35-55 peptide.
Figure 5B:
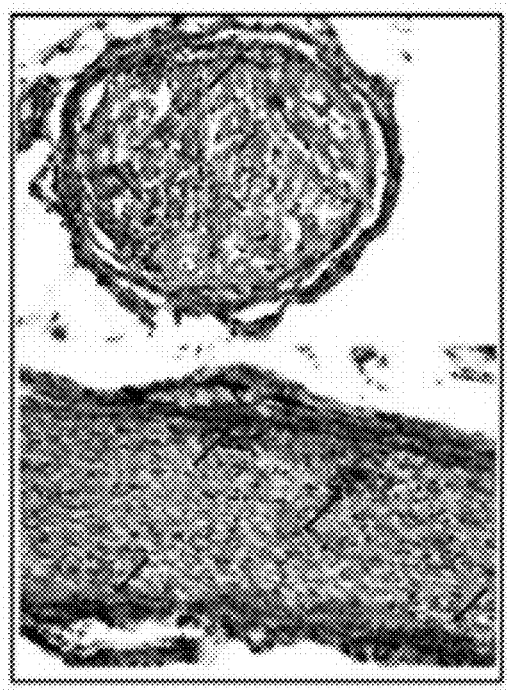

Therapeutic Effect on Inflammation in Chronic ON in HLA-DR2 Mice:

MOG immunization induced ON of a chronic nature, and the inflammatory lesions in the optic nerve correlated with the lesions in the spinal cord. FIGS. 5A and B show that HLA-DR2 mice given MOG peptide developed chronic inflammation of the optic nerve that occurred on PI days 8 to 9, before the onset of EAE (which occurred at days 11-12 PI), with inflammatory infiltrates in the optic nerve at onset on the long and cross sections stained with H&E. The incidence was 100%.

Figure 5C:
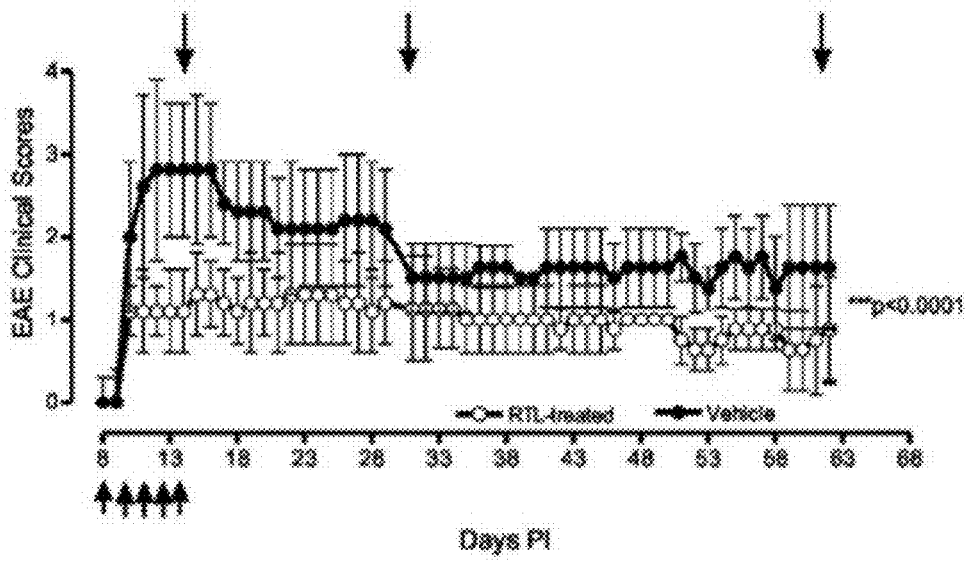
Figure 5D:
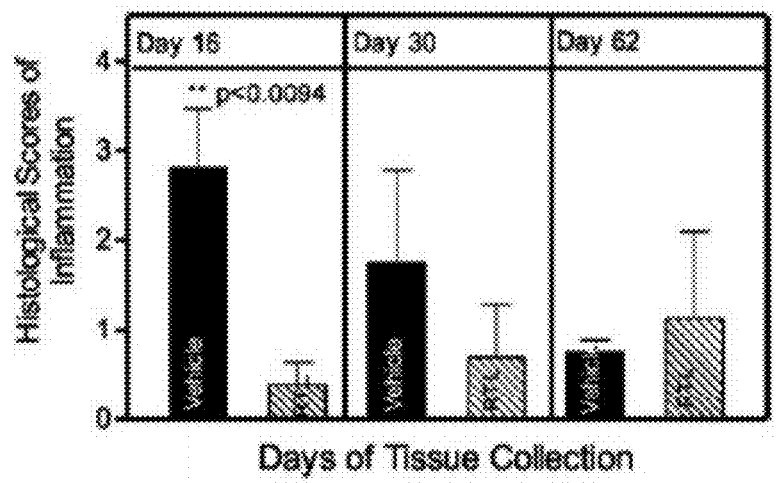
Figure 6:
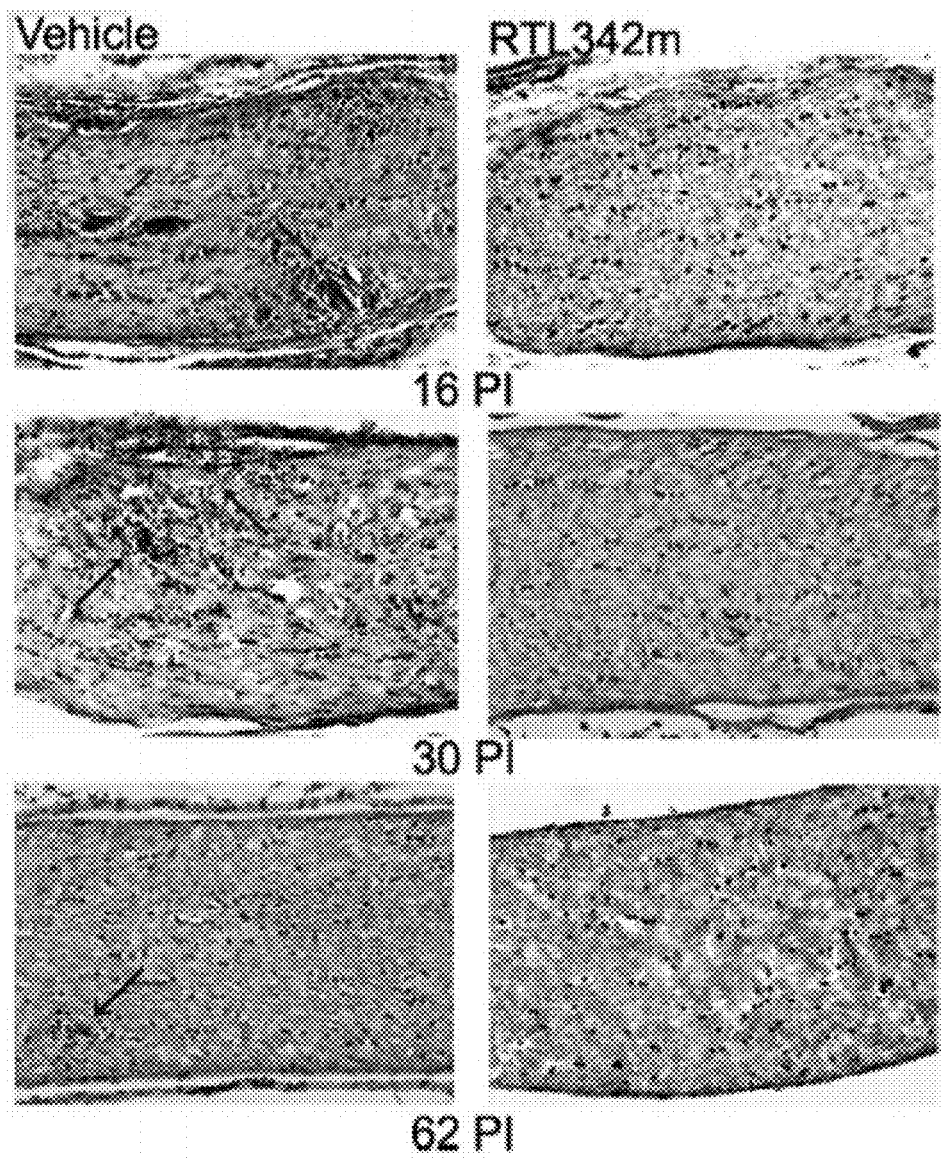
FIG. 6 is a series of digital images of histopathology of HLA-DR2 mouse optic nerves collected on days 16, 30, and 62 PI in vehicle- (left) and RTL342M-treated (right) mice. Long sections of optic nerves were stained with H&E. Arrows indicate inflammatory lesions.

To evaluate the effectiveness of RTL342M therapy administered at the onset of ON, the tissues were collected from treated and control mice on days 16 (peak), 30, and 62 PI. The treatment of the mice with five consecutive daily doses of RTL342M by subcutaneous administration at onset of ON (day 8) significantly suppressed development of histologic ON for the first 30 days and reduced inflammatory cell infiltrates in optic nerves (FIG. 6). The clinical scoring for EAE was performed daily and is shown in FIG. 5C from a representative experiment. FIG. 5D shows that the severity of ON was significantly reduced on day 16 PI with an average inflammatory score of 0.4±0.24 for treated optic nerves compared with 2.8±0.66 for the controls (P<0.0094). After treatment stopped, this effect was later diminished, and the mice presented signs of ON progression. The results suggest that, although RTL342M was effective in stopping the influx of inflammatory cells, additional doses of RTL may be needed to inhibit further development of inflammation, to reach full therapeutic benefit in those mice.

Inhibition of Myelin Loss in Optic Nerves:

The next experiment examined the effect of RTL342M on myelin loss in optic nerves. Demyelination of the optic nerve occurred around the time of inflammation, as determined by Luxol fast blue staining (FIGS. 7A-C). Myelin in normal untreated mice was nicely compact within the nerve, whereas mice with inflammation exhibited patchy loss of myelin (FIGS. 7B and C). Moreover, the loss of myelin was profound around inflammatory lesions and was progressive in untreated mice over the 62-day observation period compared with that in normal optic nerves (P<0.001). FIG. 7D shows that although the mice lost myelin due to inflammation, RTL342M protected long-term demyelination of the optic nerve compared with the control, vehicle-treated mice (days 30 and 62 PI).

FIG. 8 shows representative early pathology in consecutive long sections of the optic nerve collected 16 days (peak) after immunization without treatment. The inflammation was associated with the influx of inflammatory cells and the accumulation of macrophages (mϕ)/microglia in inflammatory lesions (arrows), as determined by immunofluorescent staining with anti-CD11b antibodies of the optic nerve (FIG. 8B). The myelin loss was apparent around inflammatory lesions, as shown using cresyl violet to counterstain the inflammatory infiltrate (FIG. 8C). In addition, early axonal damage near inflammatory cells in optic nerves was revealed by immunostaining with anti-axon RT97 antibodies (FIG. 8D) and by Bielschowsky silver impregnation of the long section of the optic nerve (FIGS. 8E and F). The cross section of the affected nerve showed axonal injury compared with healthy looking axons in normal optic nerve (FIGS. 8G and H). Together, these results from the peak of ON indicate that inflammation had an effect on myelin and axonal loss.

Quantitative analysis of Luxol fast blue-stained myelin evaluated at 30 and 62 days PI revealed that RTL342M slowed, and may even have reversed, myelin loss compared with vehicle treatment (FIG. 7D). Next, whether myelin recovery occurred after the initial loss due to inflammation and damage to the oligodendrocytes in optic nerves was examined. The long sections were immunolabeled with anti-MOG antibodies, markers for oligodendrocytes, and RT97 antibodies to label axons. FIG. 9 shows an increase in immunofluorescent labeling of MOG$^+$ (white arrows) in the RTL-treated optic nerve on day 62 PI compared with vehicle-treated mice, which showed visibly fewer immunolabeled cells (FIG. 9A). Double immunofluorescent labeling with anti-CD11b and anti-MOG antibodies revealed a greater presence of mϕ/microglia (yellow arrows) in untreated optic nerve, whereas the RTL-treated optic nerve showed a reduction in microglia and an increase in MOG-stained cells (FIG. 9B). This lack of overlapping colors showing separated staining of microglia and MOG labeling may suggest oligodendrocyte recovery rather than an increase in microglia phagocytizing myelin from damaged cells. Also, there was a substantial increase in immunofluorescence of RT97-labeled axons at day 30 PI in contrast to those in vehicle controls. These findings strongly suggest oligodendrocyte regeneration and an increase in myelin in the optic nerve after initial degeneration (30 PI) due to inflammatory processes.

Figure 10A:
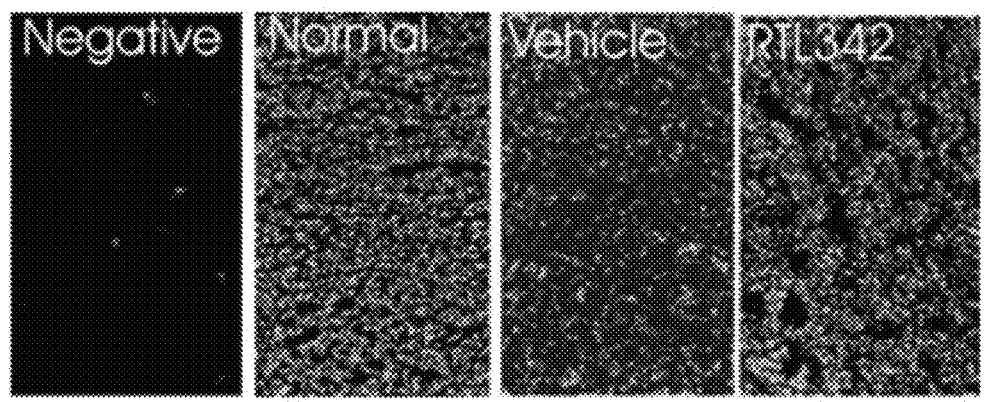
FIG. 10A-E is a series of panels showing labeling of surviving axons and RGCs in the optic nerve from vehicle- and RTL342M-treated mice.
Figure 10B:
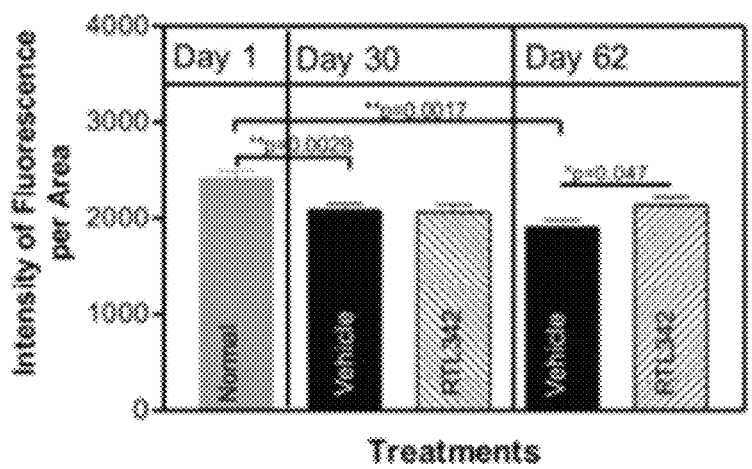
Figure 10C:
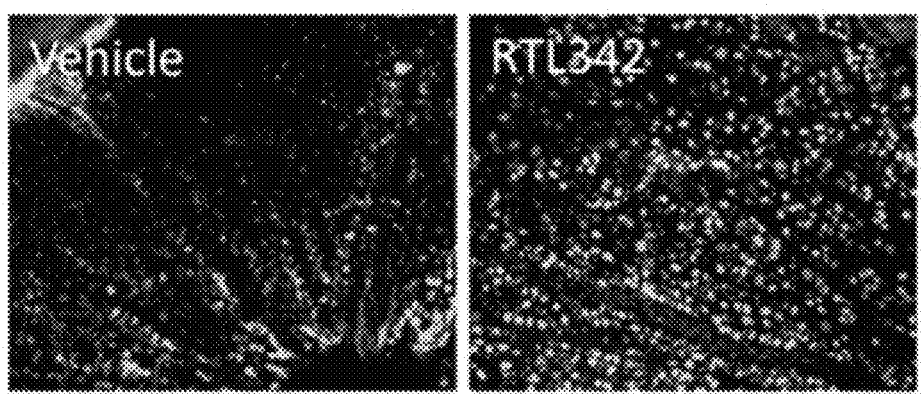
Figure 10D:
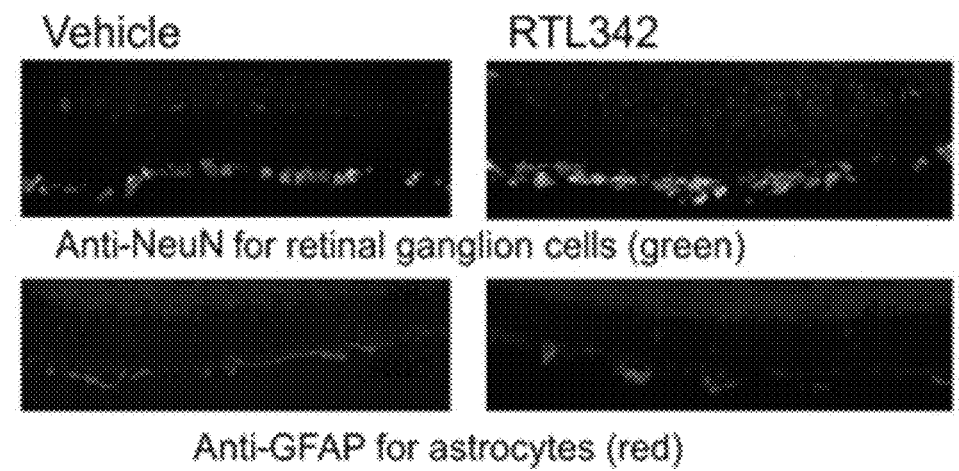
Figure 10E:
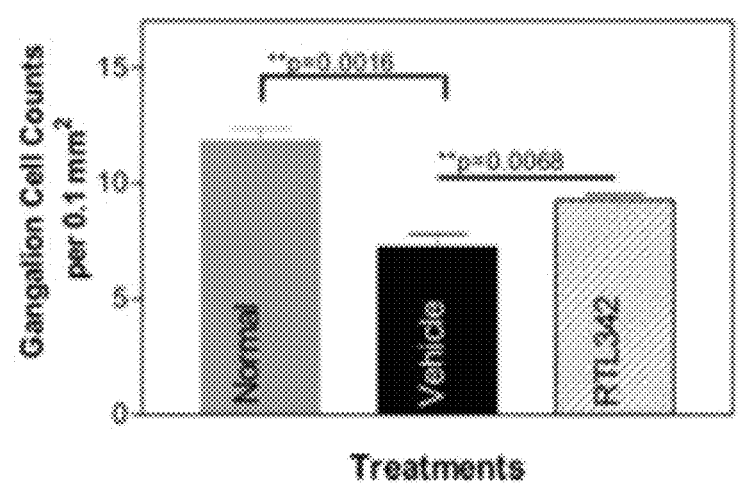

Protection from Axonal Degeneration:

As shown in FIGS. 6 and 7, inflammation and demyelination of the optic nerve were associated with progressive axonal loss. RGCs and axons that comprise the optic nerve were analyzed. FIG. 10A shows immunofluorescent axonal immunolabeling in the optic nerves at 62 PI by RT97 antibodies, which label neurofilaments. Normal optic nerves showed densely labeled axons (FIG. 10A), but the area of axonal immunofluorescent staining decreased in vehicle-treated optic nerves and showed a significant trend (FIG. 10B). Some mice were fully protected by RTL342M, but other mice still showed signs of inflammation, and in those mice, there was more myelin loss and more neuronal damage. FIG. 10B shows averaged results from both groups of mice and compared to the axonal immunolabeling for day 30 PI. In RTL342M-treated nerves at 62 PI, the number of labeled axons was significantly greater than in the vehicle-treated optic nerves (P=0.047), suggesting neuroprotection. To further examine the axonal degeneration, RGCs were analyzed by preparing retinal whole mounts and retinal cross sections obtained from day 62 PI RTL342M- and vehicle-treated mice. The retinas were immunofluorescently labeled with anti-RGC antibodies against neuron specific nuclear protein (NeuN). All retinal whole mounts from vehicle-treated mice showed a noticeable decline in the number of immunolabeled RGCs, compared with the count in RTL342M-treated mice (FIG. 10C), but analysis of the fluorescent cell count showed no statistical significance. An additional experiment of immunolabeling of RGCs with anti-NeuN antibodies on retinal cross sections also demonstrated a marked loss of RGCs in vehicle-treated retinas, which showed statistical significance (P=0.068; FIG. 10E). Immunolabeling with anti-GFAP antibodies specific for astrocytes revealed an increase in astrocyte labeling in vehicle-treated retinas in the ganglion cell layer (FIG. 10D) in contrast to RTL342M-treated retinas where more RGCs and fewer astrocytes were immunolabeled in the ganglion cell layer. These findings further suggest the protection of RGCs and their axons by the RTL treatment.

Example 7

Treatment of Optic Neuritis with RTLs

This example describes exemplary methods for treating optic neuritis in a subject and exemplary methods for assessing efficacy of RTLs for treating optic neuritis in a subject. However, one of skill in the art will appreciate that methods that deviate from these specific methods can also be used to treat optic neuritis in a subject.

Subjects having optic neuritis are selected. Subjects are treated weekly (for example, by subcutaneous injection) with an RTL (for example for 1, 2, 4, 8, 12, 18, 24, or more weeks), for example, an MHC class II β1α1 polypeptide covalently linked to an antigen of the central or peripheral nervous system (such as MOG, for example, MOG 35-55) or other RTLs as disclosed herein, at doses of 0.1 mg/kg to 25 mg/kg. Subjects are assessed for measures of visual or retinal function, such as (such as visual acuity, visual field, electroretinogram, OCT, Amsler grid, fundus examination, color vision test, or fluorescein angiography), prior to initiation of therapy, periodically during the period of therapy, and/or at the end of the course of treatment.

The effectiveness of RTL therapy to treat or inhibit optic neuritis in a subject can be demonstrated by an improvement in one or more measures of visual or retinal function or a decrease in one or more symptoms of optic neuritis, for example, compared to an untreated subject with optic neuritis, a subject with optic neuritis prior to treatment (for example, the same subject prior to treatment), or a subject with optic neuritis treated with placebo (e.g., vehicle only).

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

We claim:

1. A method for treating a disorder selected from a retinal disorder and optic neuritis in a subject, comprising:
   selecting a subject with a retinal disorder or optic neuritis, wherein the subject does not have uveitis or multiple sclerosis; and
   administering to the subject a therapeutically effective amount of a major histocompatibility complex MHC molecule comprising covalently linked first, second, and third domains, wherein the first domain is an MHC class II β1 domain and the second domain is an MHC Class II α1 domain, wherein the amino terminus of the α1 domain is covalently linked to the carboxy terminus of the β1 domain, wherein the MHC molecule does not comprise an MHC class II α2 domain or an MHC Class II β2 domain;
   wherein the third domain is covalently linked to the first domain, and wherein the third domain comprises an antigenic determinant from a retinal antigen or a myelin protein,
   thereby treating the retinal disorder or optic neuritis.

2. The method of claim 1, wherein the disorder comprises a retinal disorder comprising retinitis pigmentosa, age-related macular degeneration, Stargardt-like macular degeneration, maculopathy, autoimmune retinopathy, diabetic retinopathy, vascular retinopathy, glaucoma, or retinal detachment.

3. The method of claim 1, wherein the disorder comprises a retinal disorder and the retinal antigen is interphotoreceptor retinoid binding protein (IRBP), arrestin, recoverin, rhodopsin, phosducin, or transducins, wherein the antigenic determinant is 5 to 30 amino acids in length and binds the MHC molecule.

4. The method of claim 3, wherein the antigenic determinant comprises IRBP 1177-1191 or arrestin 291-310.

5. The method of claim 4, wherein the antigenic determinant comprises or consists of the amino acid sequence set forth as SEQ ID NO: 2 or SEQ ID NO: 3.

6. The method of claim 1, wherein the disorder comprises optic neuritis and the antigenic determinant is from a myelin protein, wherein the antigenic determinant is 8 to 30 amino acids in length and binds the MHC molecule.

7. The method of claim 6, wherein the myelin protein is myelin oligodendrocyte glycoprotein (MOG), myelin basic protein (MBP), or proteolipid protein (PLP).

8. The method of claim 7, wherein the antigenic determinant comprises or consists of MOG 35-55, MOG 1-25, MOG 94-116, MOG 145-160, MOG 194-208, MBP 85-99, MBP 145-164, PLP 139-151, or PLP 95-116.

9. The method of claim 8, wherein the antigenic determinant comprises or consists of the amino acid sequence set forth as one of SEQ ID NOs: 9-17 and 20.

10. The method of claim 1, wherein the covalent linkage between the first domain and the second domain comprises a polypeptide linker sequence.

11. The method of claim 1, wherein the covalent linkage between the first domain and the third domain comprises a polypeptide linker sequence or a disulfide bond.

12. The method of claim 1, wherein the MHC molecule comprises a human MHC molecule.

13. The method of claim 1, wherein the first domain is an MHC class II β1 domain and the second domain is an MHC class II α1 domain, wherein the amino terminus of the α1 domain is covalently linked to the carboxy terminus of the β1 domain and wherein the MHC molecule does not comprise an MHC class II α2 domain or an MHC Class II β2 domain.

14. The method of claim 13, wherein the MHC molecule comprises an HLA-DR, HLA-DP, or HLA-DQ MHC molecule.

15. The method of claim 14, wherein the MHC molecule is modified by substitution of one or more hydrophobic amino acids within a β-sheet platform of the MHC molecule, such that the MHC molecule exhibits reduced aggregation in solution compared to aggregation exhibited by an unmodified MHC molecule with a wild-type β-sheet platform.

16. The method of claim 15, wherein the MHC Class II component comprises the α1 and β1 domains of an HLA-DR protein, and wherein the one or more hydrophobic amino acids are selected from V6, I8, A10, F12, L14, and a combination of two or more thereof of the MHC class II α1 domain, and wherein the one or more hydrophobic amino acids are substituted with a non-hydrophobic amino acid.

17. The method of claim 16, wherein all of V6, I8, A10, F12, and L14 are substituted with a non-hydrophobic amino acid.

18. The method of claim 15, wherein the non-hydrophobic amino acid is a polar or a charged amino acid.

19. The method of claim 18, wherein the non-hydrophobic amino acid is serine or aspartic acid.

20. The method of claim 1, further comprising measuring visual function, retinal function, or retinal structure of the subject.

21. The method of claim 1, further comprising administering to the subject a second therapy for the retinal disorder or optic neuritis that is not an MHC molecule.

* * * * *

SEQUENCE LISTING

```
<160> NUMBER OF SEQ ID NOS: 20

<210> SEQ ID NO 1
<211> LENGTH: 216
<212> TYPE: PRT
<213> ORGANISM: Artificial Sequence
<220> FEATURE:
<223> OTHER INFORMATION: Synthetic RTL1000 polypeptide

<400> SEQUENCE: 1

Met Gly Asp Thr Arg Met Glu Val Gly Trp Tyr Arg Pro Pro Phe Ser
1               5                   10                  15

Arg Val Val His Leu Tyr Arg Asn Gly Lys Gly Gly Gly Ser Leu
                20                  25                  30

Val Pro Arg Gly Ser Gly Gly Gly Pro Arg Phe Leu Trp Gln Pro
            35                  40                  45

Lys Arg Glu Cys His Phe Phe Asn Gly Thr Glu Arg Val Arg Phe Leu
    50                  55                  60

Asp Arg Tyr Phe Tyr Asn Gln Glu Glu Ser Val Arg Phe Asp Ser Asp
65                  70                  75                  80

Val Gly Glu Phe Arg Ala Val Thr Glu Leu Gly Arg Pro Asp Ala Glu
                85                  90                  95

Tyr Trp Asn Ser Gln Lys Asp Ile Leu Glu Gln Ala Arg Ala Ala Val
                100                 105                 110

Asp Thr Tyr Cys Arg His Asn Tyr Gly Val Val Glu Ser Phe Thr Val
            115                 120                 125

Gln Arg Arg Val Ile Lys Glu Glu His Asp Ile Asp Gln Asp Glu Asp
        130                 135                 140

Tyr Asp Asn Pro Asp Gln Ser Gly Glu Phe Met Phe Asp Phe Asp Gly
145                 150                 155                 160

Asp Glu Ile Phe His Val Asp Met Ala Lys Lys Glu Thr Val Trp Arg
                165                 170                 175

Leu Glu Glu Phe Gly Arg Phe Ala Ser Phe Glu Ala Gln Gly Ala Leu
                180                 185                 190

Ala Asn Ile Ala Val Asp Lys Ala Asn Leu Glu Ile Met Thr Lys Arg
            195                 200                 205

Ser Asn Tyr Thr Pro Ile Thr Asn
        210                 215

<210> SEQ ID NO 2
<211> LENGTH: 15
<212> TYPE: PRT
```

```
<213> ORGANISM: Artificial Sequence
<220> FEATURE:
<223> OTHER INFORMATION: IRBP 1177-1191 peptide

<400> SEQUENCE: 2

Ala Asp Gly Ser Ser Trp Glu Gly Val Gly Val Val Pro Asp Val
1               5                   10                  15

<210> SEQ ID NO 3
<211> LENGTH: 20
<212> TYPE: PRT
<213> ORGANISM: Artificial Sequence
<220> FEATURE:
<223> OTHER INFORMATION: Arrestin 291-310 peptide

<400> SEQUENCE: 3

Asn Arg Glu Arg Arg Gly Ile Ala Leu Asp Gly Lys Ile Lys His Glu
1               5                   10                  15

Asp Thr Asn Leu
            20

<210> SEQ ID NO 4
<211> LENGTH: 32
<212> TYPE: PRT
<213> ORGANISM: Artificial Sequence
<220> FEATURE:
<223> OTHER INFORMATION: Phosducin 65-96 peptide

<400> SEQUENCE: 4

Lys Glu Arg Met Ser Arg Lys Met Ser Ile Gln Glu Tyr Glu Leu Ile
1               5                   10                  15

His Gln Asp Lys Glu Asp Glu Gly Cys Leu Arg Lys Tyr Arg Arg Gln
            20                  25                  30

<210> SEQ ID NO 5
<211> LENGTH: 5
<212> TYPE: PRT
<213> ORGANISM: Artificial Sequence
<220> FEATURE:
<223> OTHER INFORMATION: Recoverin 48-52 peptide

<400> SEQUENCE: 5

Gln Phe Gln Ser Ile
1               5

<210> SEQ ID NO 6
<211> LENGTH: 7
<212> TYPE: PRT
<213> ORGANISM: Artificial Sequence
<220> FEATURE:
<223> OTHER INFORMATION: Recoverin 64-70 peptide

<400> SEQUENCE: 6

Lys Ala Tyr Ala Gln His Val
1               5

<210> SEQ ID NO 7
<211> LENGTH: 20
<212> TYPE: PRT
<213> ORGANISM: Artificial Sequence
<220> FEATURE:
<223> OTHER INFORMATION: Recoverin 62-81 peptide

<400> SEQUENCE: 7

Pro Lys Ala Tyr Ala Gln His Val Phe Arg Ser Phe Asp Ala Asn Ser
1               5                   10                  15
```

Asp Gly Thr Leu
        20

<210> SEQ ID NO 8
<211> LENGTH: 14
<212> TYPE: PRT
<213> ORGANISM: Artificial Sequence
<220> FEATURE:
<223> OTHER INFORMATION: Recoverin 149-162 peptide

<400> SEQUENCE: 8

Glu Lys Arg Ala Glu Lys Ile Trp Ala Ser Phe Gly Lys Lys
1               5                   10

<210> SEQ ID NO 9
<211> LENGTH: 21
<212> TYPE: PRT
<213> ORGANISM: Artificial Sequence
<220> FEATURE:
<223> OTHER INFORMATION: MOG 35-55 peptide

<400> SEQUENCE: 9

Met Glu Val Gly Trp Tyr Arg Pro Pro Phe Ser Arg Val Val His Leu
1               5                   10                  15

Tyr Arg Asn Gly Lys
        20

<210> SEQ ID NO 10
<211> LENGTH: 20
<212> TYPE: PRT
<213> ORGANISM: Artificial Sequence
<220> FEATURE:
<223> OTHER INFORMATION: MOG 1-25 peptide

<400> SEQUENCE: 10

Gly Gln Phe Arg Val Ile Gly Pro Arg His Pro Ile Arg Ala Leu Val
1               5                   10                  15

Gly Asp Glu Val
        20

<210> SEQ ID NO 11
<211> LENGTH: 23
<212> TYPE: PRT
<213> ORGANISM: Artificial Sequence
<220> FEATURE:
<223> OTHER INFORMATION: MOG 94-116 peptide

<400> SEQUENCE: 11

Gly Gly Phe Thr Cys Phe Phe Arg Asp His Ser Tyr Gln Glu Glu Ala
1               5                   10                  15

Ala Met Glu Leu Lys Val Glu
        20

<210> SEQ ID NO 12
<211> LENGTH: 16
<212> TYPE: PRT
<213> ORGANISM: Artificial Sequence
<220> FEATURE:
<223> OTHER INFORMATION: MOG 145-160 peptide

<400> SEQUENCE: 12

Val Phe Leu Cys Leu Gln Tyr Arg Leu Arg Gly Lys Leu Arg Ala Glu
1               5                   10                  15

-continued

<210> SEQ ID NO 13
<211> LENGTH: 15
<212> TYPE: PRT
<213> ORGANISM: Artificial Sequence
<220> FEATURE:
<223> OTHER INFORMATION: MOG 194-208 peptide

<400> SEQUENCE: 13

Leu Val Ala Leu Ile Ile Cys Tyr Asn Trp Leu His Arg Arg Leu
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: MBP 85-99 peptide

<400> SEQUENCE: 14

Glu Asn Pro Val Val His Phe Phe Lys Asn Ile Val Thr Pro Arg
1               5                   10                  15

<210> SEQ ID NO 15
<211> LENGTH: 20
<212> TYPE: PRT
<213> ORGANISM: Artificial Sequence
<220> FEATURE:
<223> OTHER INFORMATION: MBP 145-164 peptide

<400> SEQUENCE: 15

Val Asp Ala Gln Gly Thr Leu Ser Lys Ile Phe Lys Leu Gly Gly Arg
1               5                   10                  15

Asp Ser Arg Ser
            20

<210> SEQ ID NO 16
<211> LENGTH: 16
<212> TYPE: PRT
<213> ORGANISM: Artificial Sequence
<220> FEATURE:
<223> OTHER INFORMATION: PLP 139-151 peptide

<400> SEQUENCE: 16

Cys His Cys Leu Gly Lys Trp Leu Gly His Pro Asp Lys Phe Val Gly
1               5                   10                  15

<210> SEQ ID NO 17
<211> LENGTH: 22
<212> TYPE: PRT
<213> ORGANISM: Artificial Sequence
<220> FEATURE:
<223> OTHER INFORMATION: PLP 95-116 peptide

<400> SEQUENCE: 17

Gly Ala Val Arg Gln Ile Phe Gly Asp Tyr Lys Thr Thr Ile Cys Gly
1               5                   10                  15

Lys Gly Leu Ser Ala Thr
            20

<210> SEQ ID NO 18
<211> LENGTH: 180
<212> TYPE: PRT
<213> ORGANISM: Artificial Sequence
<220> FEATURE:
<223> OTHER INFORMATION: Human MHC class II beta1-alpha1 RTL

<400> SEQUENCE: 18

```
Met Gly Asp Thr Arg Pro Arg Phe Leu Trp Gln Pro Lys Arg Glu Cys
1               5                   10                  15

His Phe Phe Asn Gly Thr Glu Arg Val Arg Phe Leu Asp Arg Tyr Phe
            20                  25                  30

Tyr Asn Gln Glu Glu Ser Val Arg Phe Asp Ser Asp Val Gly Glu Phe
        35                  40                  45

Arg Ala Val Thr Glu Leu Gly Arg Pro Asp Ala Glu Tyr Trp Asn Ser
    50                  55                  60

Gln Lys Asp Ile Leu Glu Gln Ala Arg Ala Val Asp Thr Tyr Cys
65                  70                  75                  80

Arg His Asn Tyr Gly Val Val Glu Ser Phe Thr Val Gln Arg Arg Val
                85                  90                  95

Ile Lys Glu Glu His Val Ile Ile Gln Ala Glu Phe Tyr Leu Asn Pro
                100                 105                 110

Asp Gln Ser Gly Glu Phe Met Phe Asp Phe Asp Gly Asp Glu Ile Phe
            115                 120                 125

His Val Asp Met Ala Lys Lys Glu Thr Val Trp Arg Leu Glu Glu Phe
        130                 135                 140

Gly Arg Phe Ala Ser Phe Glu Ala Gln Gly Ala Leu Ala Asn Ile Ala
145                 150                 155                 160

Val Asp Lys Ala Asn Leu Glu Ile Met Thr Lys Arg Ser Asn Tyr Thr
                165                 170                 175

Pro Ile Thr Asn
            180

<210> SEQ ID NO 19
<211> LENGTH: 185
<212> TYPE: PRT
<213> ORGANISM: Artificial Sequence
<220> FEATURE:
<223> OTHER INFORMATION: Mouse MHC Class II beta1-alpha1 RTL

<400> SEQUENCE: 19

Met Gly Gly Asp Ser Glu Arg His Phe Val His Gln Phe Lys Gly Glu
1               5                   10                  15

Cys Tyr Phe Thr Asn Gly Thr Gln Arg Ile Arg Leu Val Thr Arg Tyr
            20                  25                  30

Ile Tyr Asn Arg Glu Glu Tyr Leu Arg Phe Asp Ser Asp Val Gly Glu
        35                  40                  45

Tyr Arg Ala Val Thr Glu Leu Gly Arg His Ser Ala Glu Tyr Tyr Asn
    50                  55                  60

Lys Gln Tyr Leu Glu Arg Thr Arg Ala Glu Leu Asp Thr Ala Cys Arg
65                  70                  75                  80

His Asn Tyr Glu Glu Thr Glu Val Pro Thr Ser Leu Arg Arg Leu Gly
                85                  90                  95

Gly Glu Asp Asp Ile Glu Ala Asp His Val Gly Phe Tyr Gly Thr Thr
            100                 105                 110

Val Tyr Gln Ser Pro Gly Asp Ile Gly Gln Tyr Thr His Glu Phe Asp
        115                 120                 125

Gly Asp Glu Leu Phe Tyr Val Asp Leu Asp Lys Lys Thr Val Trp
    130                 135                 140

Arg Leu Pro Glu Phe Gly Gln Leu Ile Leu Phe Glu Pro Gln Gly Gly
145                 150                 155                 160

Leu Gln Asn Ile Ala Ala Glu Lys His Asn Leu Gly Ile Leu Thr Lys
                165                 170                 175
```

```
Arg Ser Asn Phe Thr Pro Ala Thr Asn
            180                 185

<210> SEQ ID NO 20
<211> LENGTH: 21
<212> TYPE: PRT
<213> ORGANISM: Artificial Sequence
<220> FEATURE:
<223> OTHER INFORMATION: Mouse MOG 35-55 peptide

<400> SEQUENCE: 20

Met Glu Val Gly Trp Tyr Arg Ser Pro Phe Ser Arg Val Val His Leu
1               5                   10                  15

Tyr Arg Asn Gly Lys
            20
```